(12) United States Patent
Srivastava

(10) Patent No.: US 7,132,109 B1
(45) Date of Patent: Nov. 7, 2006

(54) USING HEAT SHOCK PROTEINS TO INCREASE IMMUNE RESPONSE

(75) Inventor: Pramod K. Srivastava, Avon, CT (US)

(73) Assignee: University of Connecticut Health Center, Farmington, CT (US)

( * ) Notice: Subject to any disclaimer, the term of this patent is extended or adjusted under 35 U.S.C. 154(b) by 0 days.

(21) Appl. No.: 09/693,643

(22) Filed: Oct. 20, 2000

(51) Int. Cl.
*A61K 35/12* (2006.01)
*A61K 39/395* (2006.01)
*A01N 37/18* (2006.01)

(52) U.S. Cl. .............................. 424/277.1; 424/184.1; 514/2

(58) Field of Classification Search ............ 514/2, 514/44; 424/93.1, 93.21, 93.6, 93.4, 184.1, 424/192.1
See application file for complete search history.

(56) References Cited

U.S. PATENT DOCUMENTS

| | | | |
|---|---|---|---|
| 5,750,119 | A | 5/1998 | Srivastava |
| 5,830,464 | A | 11/1998 | Srivastava |
| 5,837,251 | A | 11/1998 | Srivastava |
| 5,935,576 | A | 8/1999 | Srivastava |
| 5,961,979 | A | 10/1999 | Srivastava |
| 5,985,270 | A | 11/1999 | Srivastava |
| 5,997,873 | A | 12/1999 | Srivastava |
| 6,017,540 | A | 1/2000 | Srivastava |
| 6,030,618 | A | 2/2000 | Srivastava |
| 6,048,530 | A | 4/2000 | Srivastava |

FOREIGN PATENT DOCUMENTS

| | | |
|---|---|---|
| WO | WO 97/06821 | 2/1997 |
| WO | WO 02/32923 | 4/2002 |

OTHER PUBLICATIONS

Evans et al (Q. J. Med 1999;92:299-307).*
Chen et al (Cancer Res. Feb. 15, 2000;60(4):1035-1042).*
Yang et al (Int. J. Cancer Nov. 12, 1999;83(4):532-40).*
Breloer et al J. Immunol Mar. 15, 1999;162(6):3141-7.*
Merriam-Webster Online (www.m-w.com).*
U.S. Appl. No. 60/377,483, filed May 2, 2002, Srivastava.
U.S. Appl. No. 60/377,484, filed May 2, 2002, Srivastava.
U.S. Appl. No. 10/126,368, filed Apr. 19, 2002, Srivastava.
U.S. Appl. No. 10/131,937, filed Apr. 25, 2002, Srivastava.
U.S. Appl. No. 10/131,961, filed Apr. 25, 2002, Srivastava.
Andersen P., 1994, Effective vaccination of mice against Mycobacterium tuberculosis infection with a soluble mixture of secreted mycobacterial proteins. Infect Immun. 62(6):2536-44.
Anthony et al., 1999, Priming of CD8+ CTL effector cells in mice by immunization with a stress protein-influenza virus nucleoprotein fusion molecule. Vaccine 28;17(4):373-83.
Asea et al., 2000, HSP70 stimulates cytokine production through a CD14-dependant pathway, demonstrating its dual role as a chaperone and cytokine. Nature Medicine 6:435-442.

Banchereau et al., 1998, Dendritic cells and the control of immunity. Nature 392:245-252. Review.
Barrios et al., 1992, Mycobacterial heat-shock proteins as carrier molecules. II: The use of the 70-kDa mycobacterial heat-shock protein as carrier for conjugated vaccines can circumvent the need for adjuvants and *Bacillus calmette* Guerin priming. Eur J Immunol. 22(6):1365-72.
Barrios et al., 1994, Heat shock proteins as carrier molecules: in vivo helper effect mediated by *Escherichia coli* GroEL and Dna K proteins requires cross-linking with antigen. Clin Exp Immunol. 98(2):229-33.
Basu et al., 2000, Necrotic but not apoptotic cell death releases heat shock proteins, which deliver a partial maturation signal to dendritic cell and activate the NF-kappa B pathway. Int Immunol. 12(11):1539-46.
Basu S, et al., 2001, CD91 is a common receptor for heat shock proteins gp96, hsp90, hsp70, and calreticulin. Immunity. 14(3):303-13.
Blander SJ, Horwitz MA., 1993, Major cytoplasmic membrane protein of *Legionella pneumophila*, a genus common antigen and member of the hsp 60 family of heat shock proteins, induces protective immunity in a guinea pig model of Legionaires' disease. J Clin Invest. 91(2):717-23.
Breloer et al., 1999, In vivo and in vitro activation of T cells after administration of Ag-negative heat shock proteins. J. Immunol. 162:3141-3147.
Chen et al., 1999, Human 60-kDa heat-shock protein: a danger signal to the innate immune system. J. Immunol. 162:3212-3219.
Craig, 1993, Chaperones: helpers along the pathways to protein folding. Science 260:1902-1903.
Del Giudice G., 1994, Hsp70: a carrier molecule with built-in adjuvanticity. Experientia 30;50(11-12):1061-6. Review.
Feng et al., Apr. 6-10, 2002, Exogenous heat shock proteins provide adjuvant effects on enhancing the immunogenicity of apoptotic tumor cells and inducing antitumor immunity. AACR 93$^{rd}$ Annual Meeting, vol. 43, Abstract #2214.

(Continued)

*Primary Examiner*—Sheela Huff
*Assistant Examiner*—C. Yaen
(74) *Attorney, Agent, or Firm*—Jones Day

(57) ABSTRACT

The present invention provides for a method of using heat shock proteins (HSPs) to amplify the immune response initiated by a vaccine. HSPs can be introduced into a subject before, concurrently, or after the administration of a vaccine. The HSPs can also be used to activate antigen presenting cells which are then introduced into a subject in conjunction with a vaccine. The HSPs used in the methods of the invention can be unbound or can be covalently or noncovalently bound to a peptide that is unrelated to the vaccine. The subject is preferably mammalian, and most preferably human. It is shown by way of example herein that HSPs induces secretion of cytokines and surface expression of antigen-presenting and co-stimulatory molecules. The invention also encompasses methods of treatment and prevention of cancer and infectious diseases in a subject.

49 Claims, 10 Drawing Sheets

OTHER PUBLICATIONS

Figure 1A:
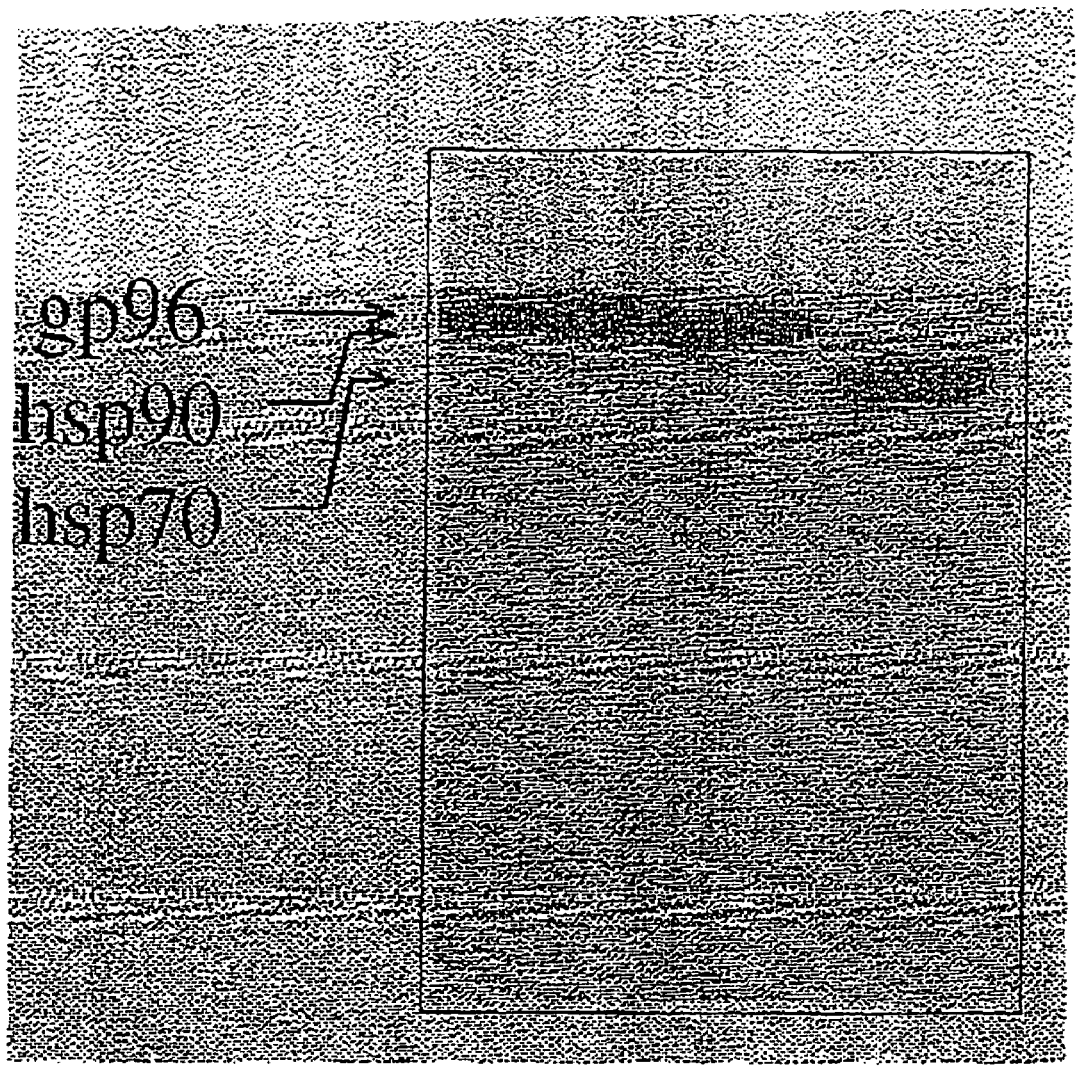

Ferrero et al., 1995, The GroES homolog of Helicobacter pylori confers protective immunity against mucosal infection in mice. Proc. Natl Acad Sci U S A. 3;92(14):6499-503.

Gallucci et al., 1999, Natural adjuvants: endogenous activators of dendritic cells. Nat. Med. 5:1249-55.

Gelber et al., 1994, Vaccination with pure *Mycobacterium leprae* proteins inhibits *M. leprae* multiplication in mouse footpads. Infect. Immun. 62(10):4250-5.

Gelber et al., 1992, Vaccination of mice with a soluble protein fraction of *Mycobacterium leprae* provides consistent and long-term protection against *M. leprae* infection. Infect Immun. 60(5):1840-4.

Gething, et al. Protein folding in the cell. Nature 1992 355:33-45. Review.

Gomez et al., 1991, Protective efficacy of a 62-kilodalton antigen, HIS-62, from the cell wall and cell membrane of *Histoplasma capsulatum* yeast cells. Infect Immun. 59(12):4459-64.

Gomez et al., 1995, Vaccination with recombinant heat shock protein 60 from *Histoplasma capsulatum* protects mice against pulmonary histoplasmosis. Infect Immun. 63(7):2587-95.

Gomez et al., 1992, An 80-kilodalton antigen from *Histoplasma capsulatum* that has homology to heat shock protein 70 induces cell-mediated immune responses and protection in mice. Infect Immun. 60(7):2565-71.

Horwitz et al., 1995, Protective immunity against tuberculosis induced by vaccination with major extracellular proteins of *Mycobacterium tuberculosis*. Proc Natl Acad Sci U S A. 92(5):1530-4.

Hubbard et al., 1992, Immunization of mice with mycobacterial culture filtrate proteins. Clin Exp Immunol. 87(1):94-8.

Janeway et al. (editors), Immuno Biology—The Immune System in Health and Disease, $3_{rd}$ Ed., Chapter 7-6, Garland Publishing Inc. New York and London (1997).

Jordan Report, 2002, Division of Microbiology and Infectious Diseases, National Institute of Allergy and Infectious Diseases, National Institutes of Health, United States.

Kojima et al., Apr. 6-10, 2002, Combination therapy of tumor-derived gp96 and GM-CSF or IL-12-gene transduced tumor cells in the control of LLC tumor. AACR $93^{rd}$ Annual Meeting, vol. 43, Abstract #5516.

Lindquist et al., 1988, The heat-shock proteins. Annu. Rev. Genetics 22:631-677. Review.

Lowrie et al., 1994, Towards a DNA vaccine against tuberculosis. Vaccine 12(16):1537-40. Review.

Lussow et al., 1991, Mycobacterial heat-shock proteins as carrier molecules. Eur J Immunol. 21(10):2297-302.

Melcher et al., 1998, Tumor immunogenicity is determined by the mechanism of cell death via induction of heat shock protein expression. Nat. Med. 5:581-7.

Menoret et al., 1995, Co-segregation of tumor immunogenicity with expression of inducible but not constitutive hsp70 in rat colon carcinomas. J. Immunol. 155:740-7.

Mizzen, 1998, Immune responses to stress proteins: applications to infectious disease and cancer. Biotherapy 10:173-185. Review.

Ohashi et al., 2000, Cutting edge: heat shock protein 60 is a putative endogenous ligand of the toll-like receptor-4 complex. J. Immunol. 164:558-561.

Pal P.G., Horwitz M.A., 1992, Immunization with extracellular proteins of *Mycobacterium tuberculosis* induces cell-mediated immune responses and substantial protective immunity in a guinea pig model of pulmonary tuberculosis. Infect Immun. 60(11):4781-92.

Pardoll, 2000, Therapeutic vaccination for cancer. Clin. Immunol. 95(1 Pt 2):S44-62.

Rescigno et al., 1998, Dendritic cell survival and maturation are regulated by different signaling pathways. J. Exp. Med. 188:2175-2180.

Sauter et al., 2000, Consequences of cell death: exposure to necrotic tumor cells, but not primary tissue cells or apoptotic cells, induces the maturation of immunostimulatory dendritic cells. J. Exp. Med. 191:423-434.

Silva C.L., Lowrie D.B., 1994, A single mycobacterial protein (hsp 65) expressed by a transgenic antigen-presenting cell vaccinates mice against tuberculosis. Immunology 82(2):244-8.

Srivastava, P.K. et al., 1991, Stress-induced proteins in immune response to cancer. Curr. Top. Microbiol. Immunol. 167:109-123, Review.

Srivastava, P.K. et al., 1998, Chromosomal assignment of the gene encoding the mouse tumor rejection antigen gp96. Immunogenetics 28:205-207.

Srivastava, P.K., 1993, Peptide-binding heat shock proteins in the endoplasmic reticulum: role in immune response to cancer and in antigen presentation. Adv. Cancer Res. 62:153-177.

Stevenson, 1999, DNA vaccines against cancer: from genes to therapy. Ann Oncol. 10:1413-8. Review.

Suto, R. et al., 1995, A mechanism for the specific immunogenicity of heat shock protein-chaperoned peptides. Science 269:1585-1588.

Suzue K., Young R.A., Heat shock proteins as immunological carriers and vaccines. in: Stress-Inducible Cellular Responses (U. Feige, R. I. Morimoto, I. Yahara, B. S. Polla, eds.), Birkhauser/Springer, 77:451-465 (1996).

Suzue K., Young R.A., 1996, Adjuvant-free hsp70 fusion protein system elicits humoral and cellular immune responses to HIV-1 p24. J Immunol. 15;156(2):873-9.

Suzue et al., 1997, Heat shock fusion proteins as vehicles for antigen delivery into the major histocompatibility complex class I presentation pathway. Proc Natl Acad Sci U S A. 25;94(24):13146-51.

Todryk et al., 1999, Heat shock protein 70 induced during tumor cell killing induces Th1 cytokines and targets immature dendritic cell precursors to enhance antigen uptake. J. Immunol. 163:1398-1408.

Udono, M., and Srivastava, P. K., 1993, Heat shock protein 70-associated peptides elicit specific cancer immunity. J. Exp. Med. 178:1391-1396.

Udono, H. et al., 1994, Comparison of tumor-specific immunogenicities of stress-induced proteins gp96, hsp90, and hsp70. J. Immunol. 152:5398-5403.

Feng et al., 2003, Exogenous stress proteins enhance the immuogenicity of apoptotic tumor cells and stimulate antitumor immunity. Blood 101(1):245-252.

Wang et al., Characterization of heat shock protein 110 and glucose-regulated protein 170 as cancer vaccines and the effect of fever-range hyperthermia on vaccine activity. J Immunol. Jan. 1, 2001;166(1):490-497.

Basu S and Srivastava PK, Calreticulin, a peptide-binding chaperone of the endoplasmic reticulum, elicits tumor- and peptide-specific immunity. J Exp Med. Mar. 1, 1999;189(5):797-802.

Elwood JM., Melanoma and sun exposure: contrasts between intermittent and chronic exposure. World J Surg. Mar.-Apr. 1992;16(2):157-165.

Egilman et al., Lung cancer and asbestos exposure: asbestosis is not necessary. Am J Ind Med. Oct. 1996;30(4):398-406.

Rozendaal et al., PCR-based high-risk HPV test in cervical cancer screening gives objective risk assessment of women with cytomorphologically normal cervical smears. Int J Cancer. Dec. 11, 1996;68(6):766-769.

Curley et al., Identification and screening of 416 patients with chronic hepatitis at high risk to develop hepatocellular cancer. Ann Surg. Sep. 1995;222(3):375-383.

Narod SA., Screening for cancer in high risk families. Clin Biochem. Aug. 1995;28(4):367-372.

Peelen et al., The majority of 22 Dutch high-risk breast cancer families are due to either BRCA1 or BRCA2. Eur J Hum Genet. 1996;4(4):225-230.

Yanagi et al., Simple and reliably sensitive diagnosis and monitoring of Philadelphia chromosome-positive cells in chronic myeloid leukemia by interphase fluorescence in situ hybridization of peripheral blood cells. Leukemia. Apr. 1999;13(4):542-552.

Tamura et al., Immunotherapy of tumors with autologous tumor-derived heat shock protein preparations. Science. Oct. 3, 1997;278(5335):117-120.

Janetzki et al., Immunization of cancer patients with autologous cancer-derived heat shock protein gp96 preparations: a pilot study. Int J Cancer. Oct. 15, 2000;88(2):232-238.

Graner et al., Tumor-derived chaperone-rich cell lysates are effective therapeutic vaccines against a variety of cancers. Cancer Immunol Immunother. Apr. 2003;52(4):226-234.

Sano et al., The augmentation of tumor-specific immunity using haptenic muramyl dipeptide (MDP) derivatives. II. Establishment of tumor-specific immunotherapy models utilizing MDP hapten-reactive helper T cell activity. Cancer Immunol Immunother. 1987;25(3):180-184.

Stack et al., Autologous x-irradiated tumour cells and percutaneous BCG in operable lung cancer. Thorax. Aug. 1982;37(8):588-593.

Wong et al., Dose-ranging study of indole-3-carbinol for breast cancer prevention. J Cell Biochem Suppl. 1997;28-29:111-116.

* cited by examiner

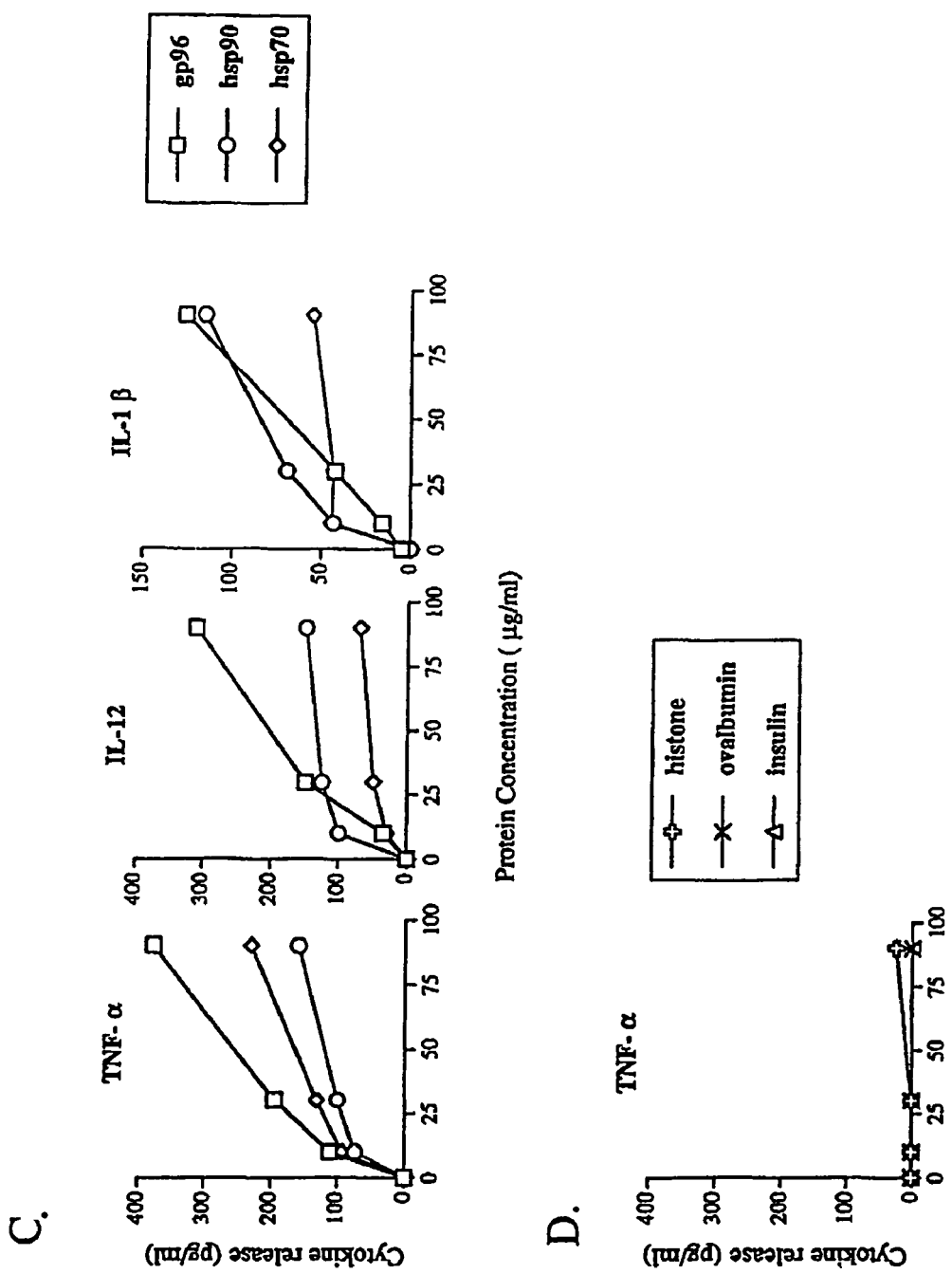
Figure 1 C,D

USING HEAT SHOCK PROTEINS TO INCREASE IMMUNE RESPONSE

1. INTRODUCTION

The present invention relates to compositions and methods of preparing immunogenic material that increases a subject's immune response to a vaccine for the prevention or treatment of cancer or infectious diseases. HSPs including, but not limited to, hsp70, hsp90 and gp96 alone or in combination with each other are administered in conjunction with a vaccine to augment the immune response of a subject against tumors and infectious agents.

2. BACKGROUND OF THE INVENTION

Citation or discussion of a reference herein shall not be construed as an admission that such is prior art to the present invention.

2.1. Vaccines

Vaccination has eradicated certain diseases such as polio, tetanus, chicken pox, and measles in many countries. This approach has exploited the ability of the immune system to resist and prevent infectious diseases.

Traditional ways of preparing vaccines include the use of inactivated or attenuated pathogens. A suitable inactivation of the pathogenic microorganism renders it harmless as a biological agent but does not destroy its immunogenicity. Injection of these "killed" particles into a host will then elicit an immune response capable of preventing a future infection with a live microorganism. However, a major concern in the use of inactivated pathogens as vaccines is the failure to inactivate all the microorganisms. Even when this is accomplished, since killed pathogens do not multiply in their host, or for other unknown reasons, the immunity achieved is often incomplete, short lived and requires multiple immunizations. Finally, the inactivation process may alter the microorganism's antigens, rendering them less effective as immunogens.

Attenuation refers to the production of strains of pathogenic microorganisms which have essentially lost their disease-producing ability. One way to accomplish this is to subject the microorganism to unusual growth conditions and/or frequent passage in cell culture. Mutants are then selected which have lost virulence but yet are capable of eliciting an immune response. Attenuated pathogens often make good immunogens as they actually replicate in the host cell and elicit long lasting immunity. However, several problems are encountered with the use of live vaccines, the most worrisome being insufficient attenuation and the risk of reversion to virulence.

An alternative to the above methods is the use of subunit vaccines. This involves immunization only with those components which contain the relevant immunological material. A new promising alternative is the use of DNA or RNA as vaccines. Such genetic vaccines have progressed from an idea to entities being studied in clinical trials (See, Weiner and Kennedy, July 1999, Scientific American, pp. 50–57).

Vaccines are often formulated and inoculated with various adjuvants. The adjuvants aid in attaining a more durable and higher level of immunity using small amounts of antigen or fewer doses than if the immunogen were administered alone. The mechanism of adjuvant action is unpredictable, complex and not completely understood (See Suzue, et al., 1996, Basel: Birkhauser Verlag, 454–55).

Because of the risks associated with inactivated and attenuated pathogens, the ability to boost or amplify an immune response to minimal quantities of a vaccine would be ideal and advantageous. Furthermore, as the mechanism of adjuvants is not completely understood and is still unpredictable, alternative methods of boosting a subject's immune response with current methods of vaccination is highly desirable.

2.2. Immune Responses

An organism's immune system reacts with two types of responses to pathogens or other harmful agents—humoral response and cell-mediated response (See Alberts, B. et al., 1994, Molecular Biology of the Cell. 1195–96). When resting B cells are activated by antigen to proliferate and mature into antibody-secreting cells, they produce and secrete antibodies with a unique antigen-binding site. This antibody-secreting reaction is known as the humoral response. On the other hand, the diverse responses of T cells are collectively called cell-mediated immune reactions. There are two main classes of T cells—cytotoxic T cells and helper T cells. Cytotoxic T cells directly kill cells that are infected with a virus or some other intracellular microorganism. Helper T cells, by contrast, help stimulate the responses of other cells: they help activate macrophages, dendritic cells and B cells, for example (See Alberts, B. et al., 1994, Molecular Biology of the Cell. 1228). Both cytotoxic T cells and helper T cells recognize antigen in the form of peptide fragments that are generated by the degradation of foreign protein antigens inside the target cell, and both, therefore, depend on major histocompatibility complex (MHC) molecules, which bind these peptide fragments, carry them to the cell surface, and present them there to the T cells (See Alberts, B. et al., 1994, Molecular Biology of the Cell. 1228). MHC molecules are typically found in abundance on antigen-presenting cells (APCs).

2.3. Antigen Presentation

Antigen-presenting cells (APCs), such as macrophages and dendritic cells, are key components of innate and adaptive immune responses. Antigens are generally 'presented' to T cells or B cells on the surfaces of other cells, the APCs. APCs can trap lymph- and blood-borne antigens and, after internalization and degradation, present antigenic peptide fragments, bound to cell-surface molecules of the major histocompatibility complex (MHC), to T cells. APCs may then activate T cells (cell-mediated response) to clonal expansion, and these daughter cells may either develop into cytotoxic T cells or helper T cells, which in turn activate B (humoral response) cells with the same MHC-bound antigen to clonal expansion and specific antibody production (See Alberts, B. et al., 1994, Molecular Biology of the Cell. 1238–45).

Two types of antigen-processing mechanisms have been recognized. The first type involves uptake of proteins through endocytosis by APCs, antigen fragmentation within vesicles, association with class II MHC molecules and expression on the cell surface. This complex is recognized by helper T cells expressing CD4. The other is employed for proteins, such as viral antigens, that are synthesized within the cell and appears to involve protein fragmentation in the cytoplasm. Peptides produced in this manner become associated with class I MHC molecules and are recognized by cytotoxic T cells expressing CD8 (See Alberts, B. et al., 1994, Molecular Biology of the Cell. 1233–34).

Stimulation of T cells involves a number of accessory molecules expressed by both T cell and APC. Co-stimulatory molecules are those accessory molecules that promote the growth and activation of the T cell. Upon stimulation, co-stimulatory molecules induce release of cytokines, such as interleukin 1 (IL-1) or interleukin 2 (IL-2), interferon, etc., which promote T cell growth and expression of surface receptors (See Paul, 1989, Fundamental Immunology. 109–10).

Normally, APCs are quiescent and require activation for their function. The identity of signals which activate APCs is a crucial and unresolved question (See Banchereau, et al., 1998, Nature 392:245–252; Medzhitov, et al., 1998, Curr Opin Immunol. 10:12–15).

2.4. Heat Shock Proteins

Heat shock proteins, also known as stress proteins, are intracellular molecules that are abundant, soluble, and highly conserved. As intracellular chaperones, HSPs participate in many biochemical pathways of protein maturation and function active during times of stress and normal cellular homeostasis (See Mizzen, 1998, Biotherapy 10:174). Many stresses can disrupt the three-dimensional structure, or molding, of a cell's proteins. Left uncorrected, mis-folded proteins form aggregates that may eventually kill the cell. HSPs bind to those damaged proteins, helping them refold into their proper conformations. In normal (unstressed) cellular homeostasis, HSPs are required for cellular metabolism. HSPs help newly synthesized polypeptides fold and thus prevent premature interactions with other proteins. Also, HSPs aid in the transport of proteins throughout the cell's various compartments.

The major HSPs can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch et al., 1985, J. Cell. Biol. 101:1198–1211). In contrast, hsp90 and hsp60 proteins are abundant at normal temperatures in most, but not all, mammalian cells and are further induced by heat (Lai et al., 1984, Mol. Cell. Biol. 4:2802–2810; van Bergen en Henegouwen et al., 1987, Genes Dev. 1:525–531).

HSPs have been found to have immunological and antigenic properties. Immunization of mice with gp96 or p84/86 isolated from a particular tumor rendered the mice immune to that particular tumor, but not to antigenically distinct tumors (Srivastava, P. K. et al., 1988, Immunogenetics 28:205–207; Srivastava, P. K. et al., 1991, Curr. Top. Microbiol. Immunol. 167:109–123). Further, hsp70 was shown to elicit immunity to the tumor from which it was isolated but not to antigenically distinct tumors. However, hsp70 depleted of peptides was found to lose its specific immunogenic activity (Udono, M., and Srivastava, P. K., 1993, J. Exp. Med. 178:1391–1396). These observations suggested that the heat shock proteins are not antigenic per se, but form noncovalent complexes with antigenic peptides, and the complexes can elicit specific immunity to the antigenic peptides (Srivastava, P. K., 1993, Adv. Cancer Res. 62:153–177; Udono, H. et al., 1994, J. Immunol., 152: 5398–5403; Suto, R. et al., 1995, Science, 269:1585–1588). Recently, hsp60 and hsp70 have been found to stimulate production of proinflammatory cytokines, such as TNFα and IL-6, by monocytes, macrophages, or cytotoxic T cells (Breloer et al., 1999, J. Immunol. 162:3141–3147; Chen et al., 1999, J. Immunol. 162:3212–3219; Ohashi et al., 2000, J. Immunol. 164:558–561; Asea et al., 2000, Nature Medicine, 6:435–442; Todryk et al., 1999, J. Immunol. 163: 1398–1408). Hsp70 has also been shown to target immature dendritic cells and make them more able to capture antigens (Todryk et al., J. Immunol. 163:1398–1408). It has been postulated that release of or induction of expression of hsp60 and hsp70, e.g., due to cell death, may serve to signal that an immune reaction should be raised (Chen et al., 1999, J. Immunol. 162:3212–3219; Ohashi et al., 2000, J. Immunol. 164:558–561; Todryk et al., 1999, J. Immunol. 163:1398–1408).

The use of noncovalent complexes of HSP and peptide, purified from cancer cells, for the treatment and prevention of cancer has been described in U.S. Pat. Nos. 5,750,119, 5,837,251, and 6,017,540.

The use of HSP-peptide complexes for sensitizing antigen presenting cells in vitro for use in adoptive immunotherapy is described in U.S. Pat. Nos. 5,985,270 and 5,830,464.

HSP-peptide complexes can also be isolated from pathogen-infected cells and used for the treatment and prevention of infection caused by the pathogen, such as viruses, and other intracellular pathogens, including bacteria, protozoa, fungi and parasites; see U.S. Pat. Nos. 5,961,979, and 6,048,530.

Immunogenic HSP-peptide complexes can also be prepared by in vitro complexing of HSPs and antigenic peptides, and the uses of such complexes for the treatment and prevention of cancer and infectious diseases has been described in U.S. Pat. Nos. 5,935,576, and 6,030,618. The use of heat shock protein in combination with a defined antigen for the treatment of cancer and infectious diseases have also been described in PCT publication WO97/06821 dated Feb. 27, 1997.

The purification of HSP-peptide complexes from cell lysate has been described previously; see for example, U.S. Pat. Nos. 5,750,119, and 5,997,873.

3. SUMMARY OF THE INVENTION

The present invention provides for a method of producing or increasing an immune response elicited by vaccines using HSPS. The source of the HSP is preferably an eukaryote, and most preferably a mammal.

In one embodiment of the invention, the method for producing an immune response comprises administering to the subject a vaccine composition comprising a component against which an immune response is desired to be induced; and administering to the subject a heat shock protein preparation, wherein the immune response against the component is not elicited in the absence of the administering of the vaccine composition. The heat shock protein preparation does not display the immunogenicity of the component. The heat shock protein preparation alone cannot elicit an immune response against the component in the absence of the administering of the vaccine composition. The method can increase the magnitude of the immune response to the component of interest relative to that obtained in the absence of administering to the subject a heat shock protein preparation.

In another embodiment, the invention provides for a method of inducing an immune response by a sub-immunogenic amount of a vaccine composition, wherein the HSP preparation facilitates the induction of an immune response by an amount of vaccine composition which is otherwise insufficient for inducing the immune response when used alone. In particular, the method comprises the steps of (a) administering to the subject an amount of a heat shock protein preparation; and (b) administering to the subject a vaccine composition comprising a component against which an immune response is desired to be induced in an amount that is sub-immunogenic in the absence of step(a), whereby an immune response to said component is induced in the subject, and wherein the heat shock protein preparation does not display the immunogenicity of the component. The heat shock protein preparation does not elicit an immune response against said component in the absence of said administering of the vaccine composition.

In yet another embodiment, the invention provides a method of treating or preventing an infectious disease in a subject comprising administering to the subject a vaccine composition comprising a component that displays the antigenicity of an infectious agent that causes the infectious disease; and administering to the subject an amount of a heat shock protein preparation effective in combination with the vaccine composition to induce or increase an immune response to the component in the subject. The heat shock protein preparation does not display the immunogenicity of the component.

In yet another embodiment, the invention provides a method of treating or preventing a cancer in a subject comprising administering to the subject a vaccine composition comprising a component that displays the antigenicity of a cancer cell; and administering to the subject an amount of a heat shock protein preparation effective to induce or increase an immune response in the subject to the component wherein the heat shock protein preparation does not display the immunogenicity of the component.

In yet another embodiment, the invention provides a method of inducing an immune response by a vaccine composition in a subject comprising administering to the subject a heat shock protein preparation; and administering to the subject a vaccine composition comprising a component against which an immune response is desired to be induced, the vaccine composition being in an amount that is sub-immunogenic for the component in the absence of the vaccine composition. The heat shock protein preparation does not display the immunogenicity of the component In yet another embodiment, the invention provides a method of activating antigen presenting cells comprising contacting APCs with a heat shock protein preparation. In particular, the antigen presenting cells can be obtained from an individual, the APCs being optionally expanded and/or purified, and treated ex vivo with a heat shock protein preparation. The treated APCs can then be administered to a subject concurrently, before, or after with the administration of a vaccine composition against which an immune response is desired to be induced. The patient may be treated according to the present invention with a vaccine composition and with activated APCs and/or an HSP preparation.

In these above-mentioned embodiments of the invention, the heat shock protein preparation does not elicit an immune response against the component in the absence of the administration of the vaccine composition. The heat shock protein preparation does not display the immunogenicity of the component in the vaccine composition. The immunogenicity of a heat shock protein preparation can be tested in vivo or in vitro by any method known in the art, such as but not limited to those described in section 5.5.

In various embodiments, the HSPs is administered into a subject before the administration of a vaccine composition. Alternatively, the HSPs is administered to the subject concurrently with the administration of a vaccine composition. The HSPs can also be administered to the subject after the administration of a vaccine composition. Preferably, the subject is mammalian, or, more specifically, human.

The present invention further provides a method for improving the outcome of a treatment in a subject receiving a therapeutic modality which is not a vaccine. The method comprises administering a mammalian heat shock protein preparation to the subject before, concurrently with, or after the administration of the therapeutic modality.

Without being bound any theory, an increased concentration of HSP induces secretion of cytokines and surface expression of antigen-presenting and co-stimulatory molecules. Applicant's experimentation with CD11b$^+$ cell activation shows that the presence of HSPs in the extracellular milieu induces interleukin-1β secretion and surface expression of MHC class II molecules. The activation of APCs increases the affinity between the resultant antigen-MHC complexes from the vaccine and T-cell antigen surface receptors (TCRs) on the surface of the T-cells. Accordingly, the HSP preparation administered to a subject can boost the effectiveness of a vaccine by increasing the efficiency and effectiveness of antigen presentation.

The HSP preparation used in the methods of the invention can include free HSP not bound to any molecule, and molecular complexes of HSP with another molecule, such as a peptide. An HSP-peptide complex comprises of a HSP covalently or noncovalently attached to a peptide. The methods of the invention does not require covalent or noncovalent attachment to any specific antigens or antigenic peptides prior to administration to a subject.

Also encompassed in the invention are kits comprising one or more containers each containing a heat shock protein preparation in an amount effective to increase an immune response elicited by a vaccine composition against a component of the vaccine composition against which an immune response is desired; and one or more containers each containing the vaccine composition in an amount that, when administered before, concurrently with, or after the administration of the heat shock protein preparation of (a), is effective to induce an immune response against the component.

4. BRIEF DESCRIPTION OF THE FIGURES

Figure 1B:
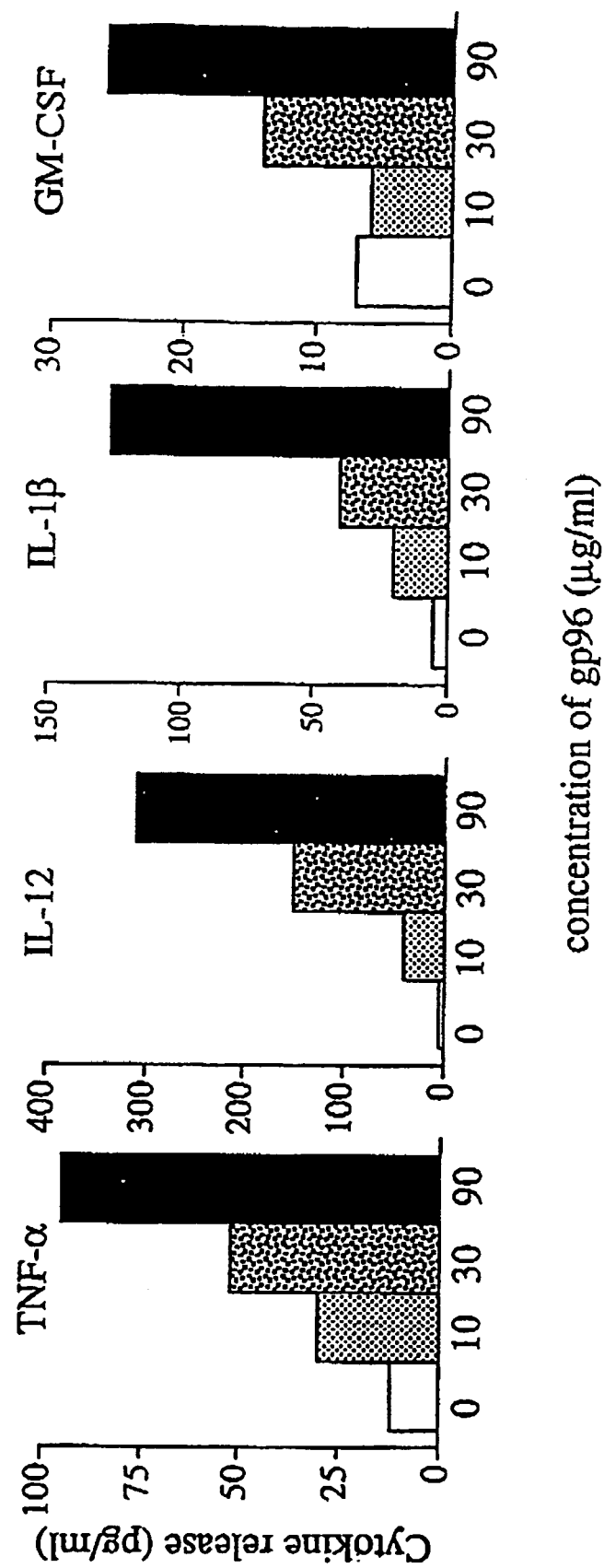

FIGS. 1A–1D. FIG. 1A. SDS-PAGE analysis of purified preparations of gp96, hsp90 and hsp70. The HSPs were purified from livers of C57BL/6 mice, as described in Section 6.1. Two μg of each HSP preparation was applied to each lane. FIG. 1B. Peritoneal cells obtained from C57BL/6 mice injected intraperitoneally with pristane were positively selected for CD11b+ cells. Cells ($5 \times 10^4$) were incubated for 20 hours at 37° C. in complete RPMI medium with 5% fetal calf serum alone, or with increasing quantities of homogenous preparation of gp96 (FIG. 1B) or hsp90 or hsp70 (FIG. 1C) purified from livers of C57BL/6 mice, as indicated, in the same medium. Supernatants were harvested and assayed by ELISA for TNF-α, IL-12, IL-1β and BM-CSF. Cultures of CD11b$^+$ cells were also similarly incubated with non-HSPs such as histone, ovalbumin and insulin and the supernatants tested for TNF-α (FIG. 1D).

Figure 2:
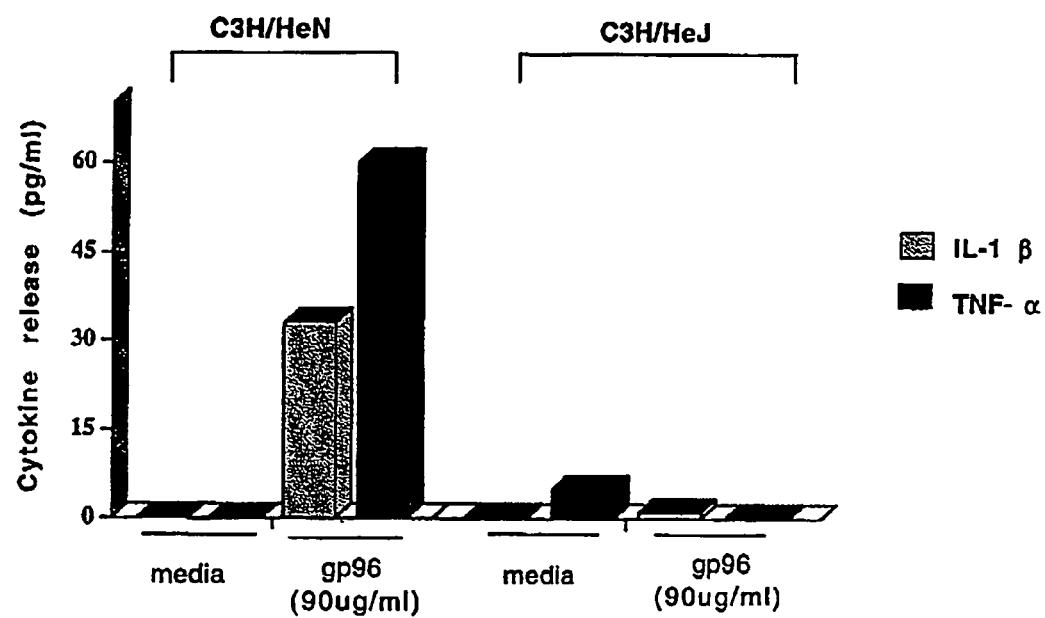

FIG. 2. The APC-stimulating activity of gp96 is abridged in an LPS-hyporesponsive mouse strain. CD11b$^+$ cells ($5 \times 10^4$), isolated from C3H/HeN or C3H/HeJ strains of mice as described in Section 6.1, were incubated in complete RPMI medium with 5% fetal calf serum alone, or treated with gp96 at the indicated amounts in the same medium for 20 hrs at 37° C. Supernatants were harvested and assayed for IL-1β and TNF-α as indicated, by ELISA.

Figure 3A:
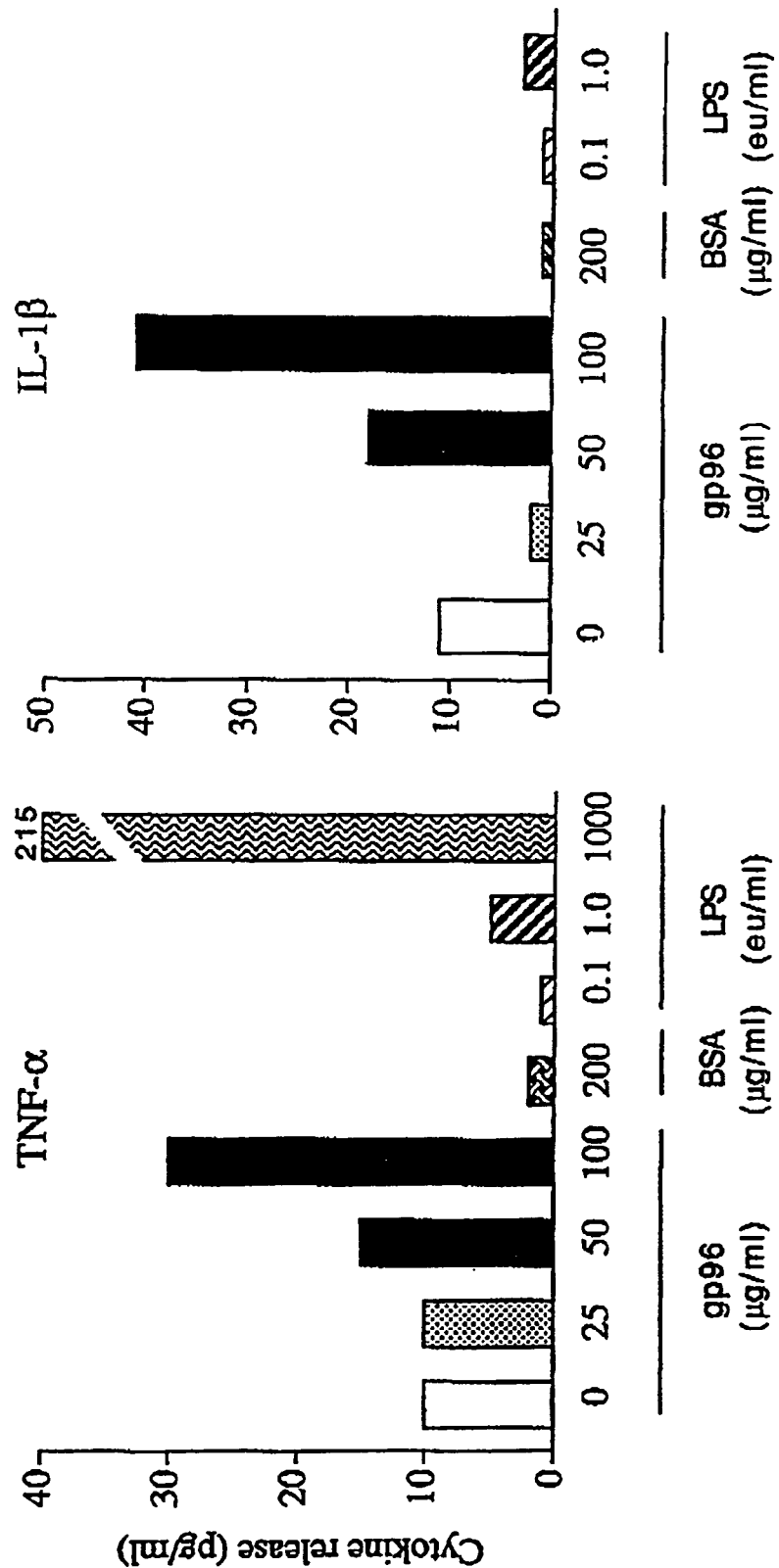
Figure 3B:
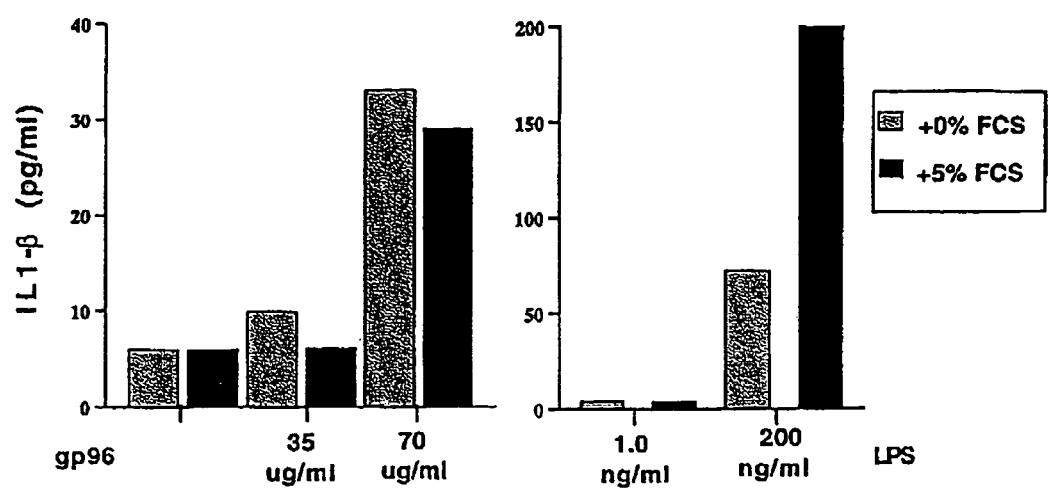
Figure 3C:
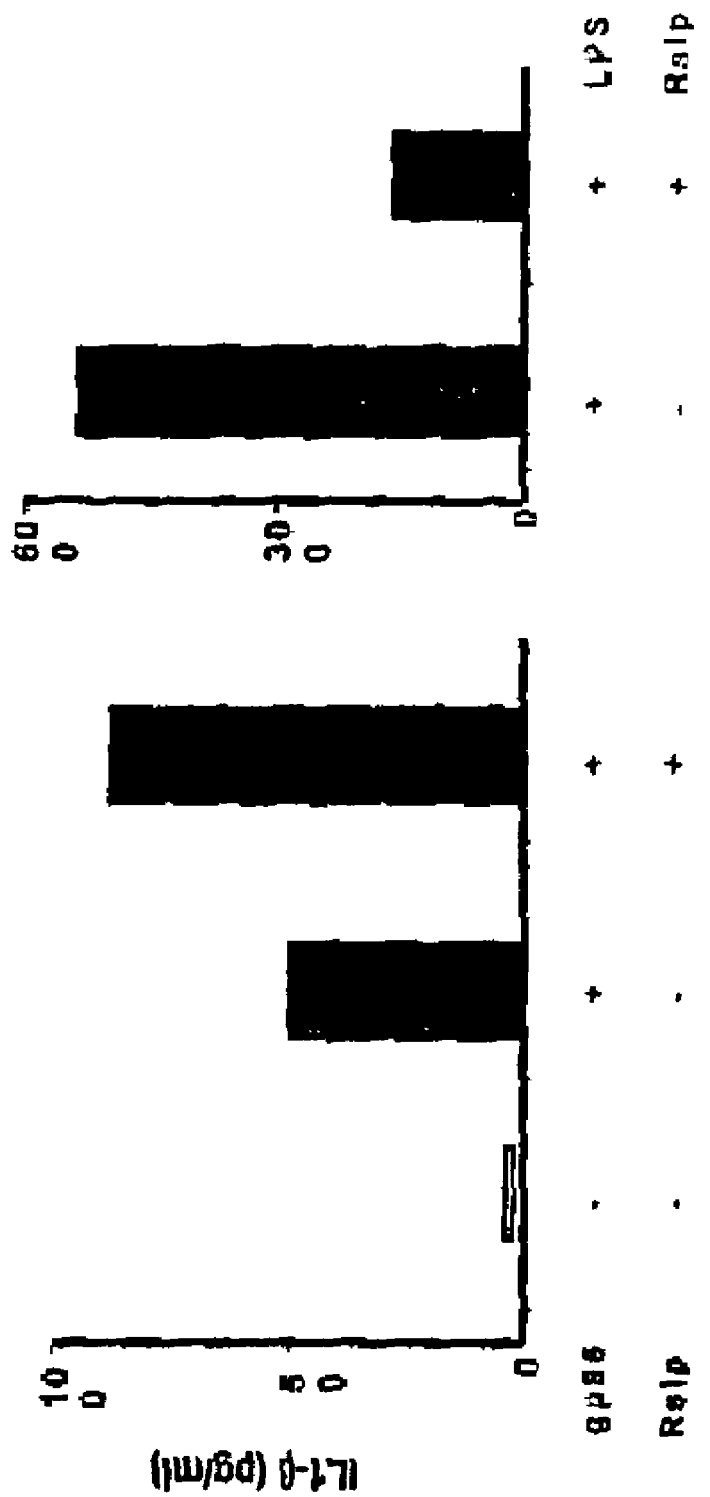

FIGS. 3A–3C. The APC-stimulating activity of gp96 does not derive from contaminating LPS. FIG. 3A. CD11b+ cells ($5\times10^4$), isolated from C57BL/6 mice as described were incubated in complete RPMI medium with 5% fetal calf serum alone, or treated with gp96, LPS or BSA at the indicated amounts in the same medium for 20 hrs at 37° C. Supernatants were harvested and assayed for IL-1β and TNF-α, as indicated by ELISA. FIG. 3B. CD11b+ cells ($5\times10^4$), isolated from C57BL/6 mice were incubated in complete RPMI medium with or without 5% fetal calf serum (as a source of LBP) as indicated, or treated with gp96 or LPS at the indicated amounts in the above media for 20 hrs at 37° C. Supernatants were harvested and assayed for IL-1 by ELISA. FIG. 3C. The LPS antagonist Rslp, derived from *Rhodopseudomonas spheroides* (2 μg/ml) was added to cytokine secretion assay of LPS (2 μg/ml) or gp96 (90 μg/ml) as indicated.

Figure 4:
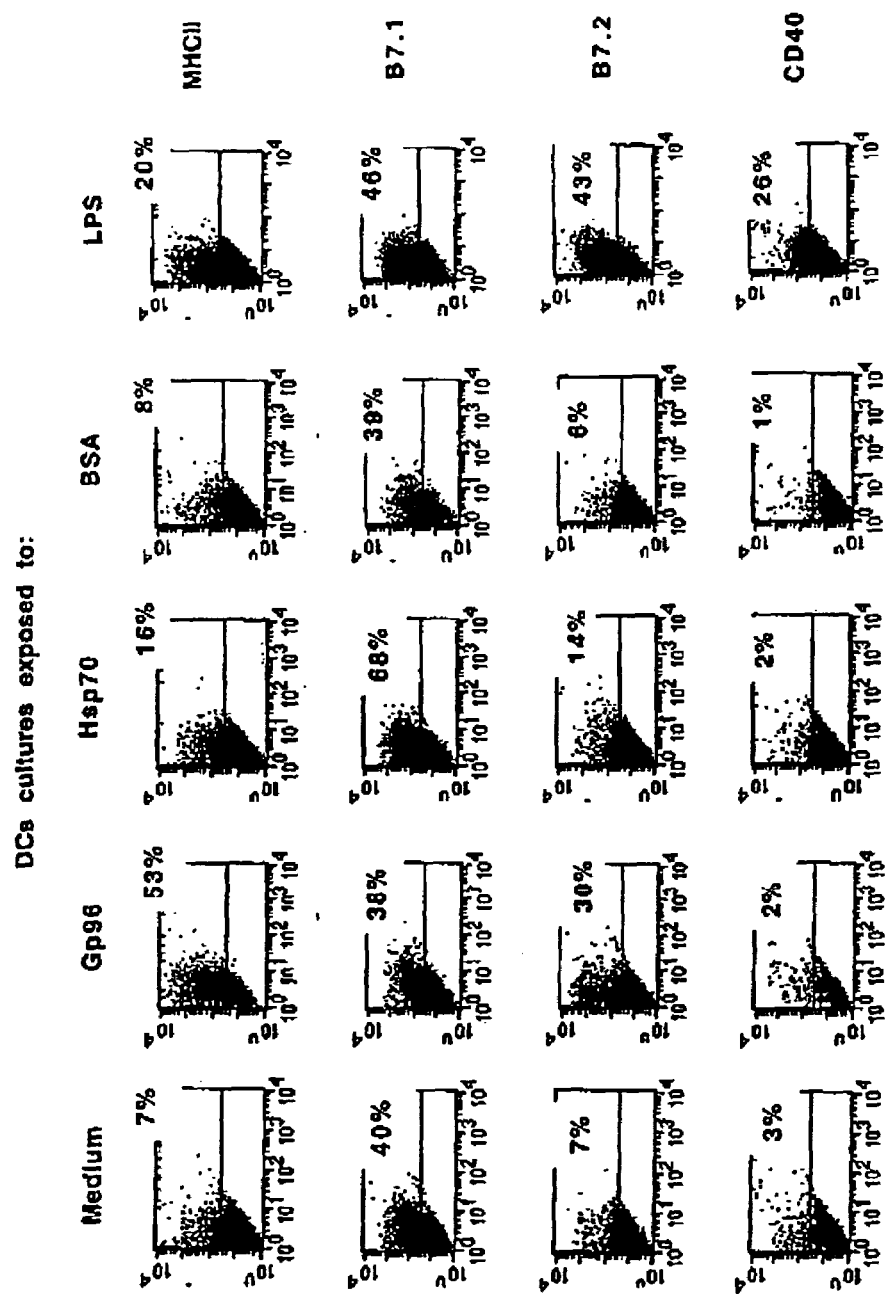

FIG. 4. HSPs stimulate CD11c+ cells to express antigen presenting and co-stimulatory molecules. Bone marrow-derived DC cultures were exposed to the medium, HSPs (400 μg/ml) or LPS (2 μg/ml) for 20 hours, harvested and analyzed for expression of the cell surface molecules indicated. GM-CSF was not present in the DC cultures when they were treated with medium alone, or gp96, or LPS or albumin. The percentages shown are CD11c+ cells that are also positive for the indicated surface markers. Cells were analyzed by flow cytometry using the FACScan (Becton Dickinson, La Jolla, Calif.). Live cells were gated based on FSC/SSC profiles.

Figure 5:
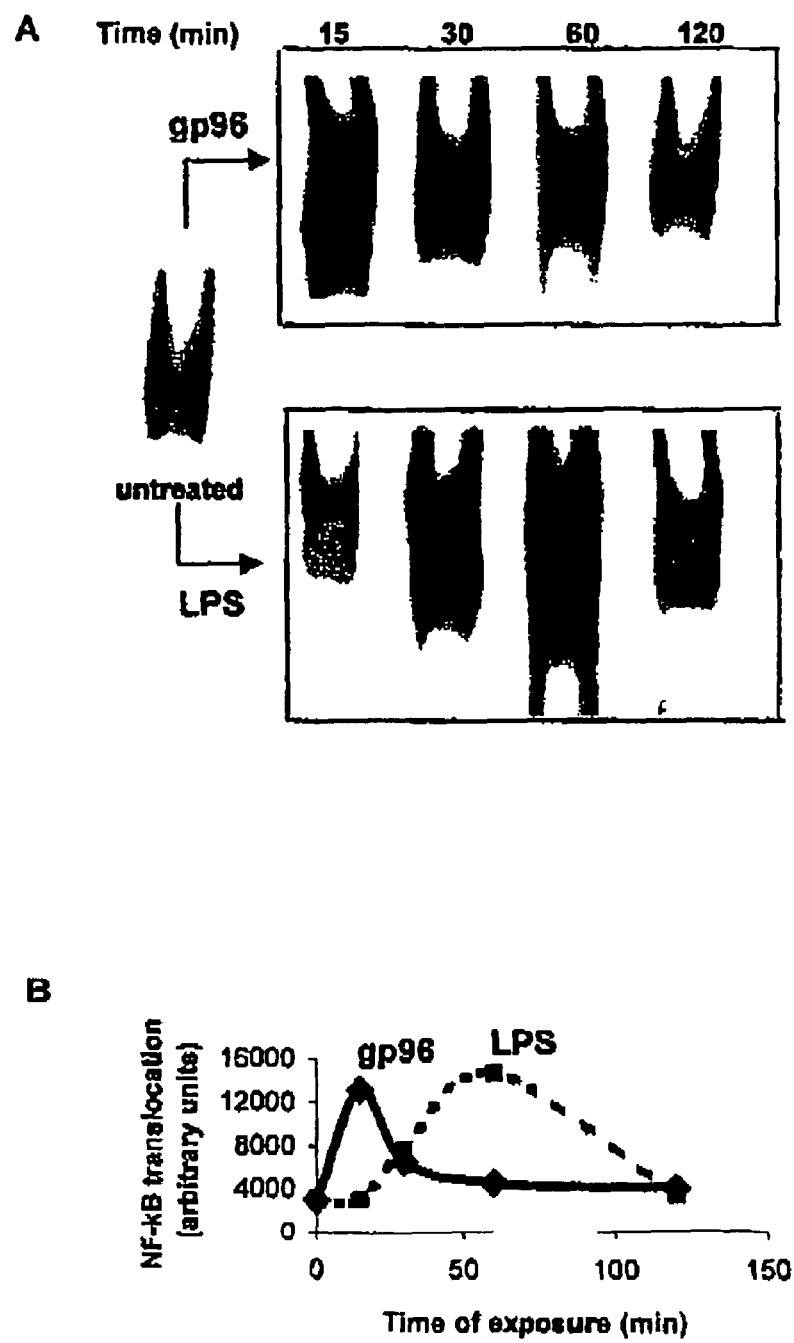

FIG. 5. Gp96 interacts with APCs through the NFκB signal transduction pathway. (A) DCs ($1\times10^6$ cells) were pulsed with gp96 (100 μg/ml) or LPS (4 μg/ml) for the indicated time points. Nuclear extracts of unpulsed or pulsed cultures were prepared and were used in binding to NFκB-specific oligomer as described in Methods. The complexes were resolved by native PAGE and autoradiographed. (B) The data from (A) are quantitated by scanning the gels under linear conditions of exposure, and plotted.

Figure 6:
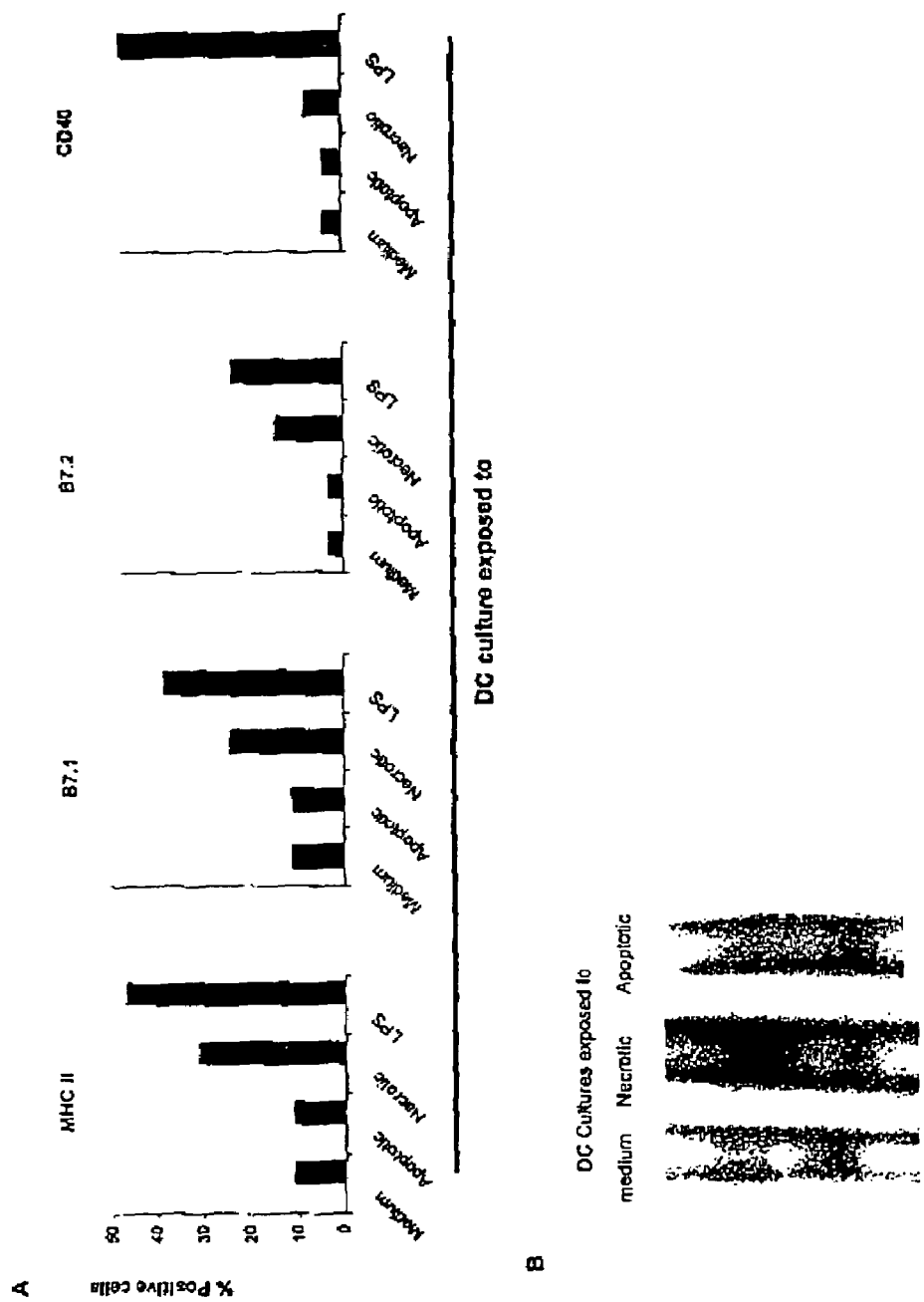

FIGS. 6A–6B. Exposure of DCs to necrotic but not apoptotic cells leads to maturation of DCs and to nuclear translocation of NFκB. (A) Cultures of immature DCs ($2\times10^6$) were pulsed with medium alone, or $10^6$ cell equivalents each of necrotic or apoptotic E.G7 cells, or LPS (as a positive control) for 20 h. DC cultures were monitored for expression of surface markers as indicated. (B) DC cultures exposed to medium alone, or to necrotic or apoptotic E.G7 cells for 15 minutes and were analyzed for translocation of NFκB as described in legend to FIG. 5.

5. DETAILED DESCRIPTION OF THE INVENTION

The present invention provides a method of producing or increasing an immune response elicited by a vaccine composition, comprising administering heat shock proteins (HSPs) in conjunction with the administration of the vaccine composition.

Some of the current vaccination strategies use attenuated viral and bacterial strains or whole cells that have been killed to induce an immune response in a subject in whom treatment or prevention of an infectious disease or cancer is desired. However, these strategies carry the risk that the attenuated strains may recombine genetically with the host DNA and turn into a virulent strain. Thus, the ability to boost or increase an immune response using the claimed method with these vaccines is desirable and advantageous. Additionally, the ability to augment or amplify a subject's immune response using the claimed method with a generally weak vaccine presents a safer and more feasible alternative to using larger dosages of the weak vaccine. The methods of the invention can also aid the induction of an immune response by an amount of vaccine composition that is insufficient to induce an immune response if used alone. The methods of the invention can be used with any type of vaccine composition comprising a component against which an immune response is desired, including but not limited to, live vaccine, attenuated vaccine, subunit vaccine, DNA vaccine, and RNA vaccine. The vaccine composition may comprise an adjuvant. The vaccine composition may be administered with one or more adjuvants.

In the present invention, an HSP preparation is administered to a subject, preferably at a site where APCs are expected to encounter the antigen(s) (molecular components against which an immune response is desired to be induced) in a vaccine composition, before, concurrently with, or after the administration of the vaccine composition. The HSP preparations of the invention activate APCs and thus, increases the effectiveness and/or the efficiency of antigen presentation. Accordingly, the present invention provides for a method of using an HSP preparation to increase a subject's immune response elicited by the vaccine composition. The activation of APCs by the HSP preparations ex vivo and the subsequent administration of activated APCs are encompassed in the present invention. Such administration of activated APCs can be carried out, before, concurrently with, or after the administration of a vaccine composition, which vaccine composition, and activated APCs, may be administered before, concurrently with, or after the administration of a HSP preparation according to the methods of the invention. Thus, a patient may be treated according to the present invention with a vaccine composition and with activated APCs and/or an HSP preparation. A HSP preparation that is the same as or different from the HSP preparation to be administered can be used for activating the APCs.

Without being bound by any theory or mechanism, the applicants believe that the HSP preparation, upon contact with APCs at a site, upregulate expression of co-stimulatory molecules on the cell surface of APCs, and increase cytokine production. Although not limited to this mechanism, increase or amplification of a subject's immune response is likely induced by the HSP's upregulation of co-stimulatory molecules and other molecules required for antigen presentation on the APCs, such as B7-1, B7-2, and MHC class II, and their ensuing increase in production of cytokines, soluble molecules that mediate interaction between cells, often promoting immune cell growth and division. Because of this HSP-induced stimulation of co-stimulatory molecules, the claimed methods generally boost T-cell activation and increase a subject's immune response. As a result, an increased number of activated APCs are available to present to T-cells antigens, including those present in a vaccine administered in the same immunological time frame. The ability of HSPs to activate APCs can confer a distinct immunological advantage to the subject. However, it should be noted that the present invention is not to be limited in scope by the mechanism described herein.

For the purposes of this invention, an HSP preparation is a composition comprising HSPs whether unbound or bound to other molecules (e.g., peptides). The HSP is preferably purified. An HSP preparation may include crude cell lysate comprising HSP, the amount of lysate corresponding to between 100 to $10^6$ cell equivalents. When a peptide is attached to a HSP, the peptide may be any peptide, which can be noncovalently or covalently bound to the HSP. Hsps can be conveniently purified from most cellular sources as a population of complexes of different peptides non-covalently bound to HSPs. The peptide(s) may be unrelated to the vaccine composition, or the infectious disease or disorder in question. The HSPs can be separated from the non-covalently bound peptides by exposure to low pH and/or adenosine triphosphate, or other methods known in the art. Generally, the HSP preparation is separately administered from the vaccine composition. For convenience and comfort of a recipient, the HSP preparation can be mixed with the vaccine composition immediately prior to administration. When the HSP preparation is not used in conjunction with a vaccine composition to elicit a specific immune response, administering the HSP preparation alone does not induce the antigen-specific immune response that would have been induced by the vaccine composition.

In various embodiments, the source of the HSP is preferably an eukaryote, more preferably a mammal, and most preferably a human. Accordingly, the HSP preparation used by the methods of the invention includes eukaryotic HSPs, mammalian HSPs and human HSPS. The eukaryotic source from which the HSP preparation is derived and the subject receiving the HSP preparation are preferably the same species.

In one embodiment, the HSP preparation is administered to a subject at reasonably the same time as the vaccine. This method provides that the two administrations are performed within a time frame of less than one minute to about five minutes, or up to about sixty minutes from each other, for example, at the same doctor's visit.

In another embodiment, the HSP preparation is administered to a subject within a time frame of one hour to twenty four hours after the administration of a vaccine. The time frame can be extended further to a few days or more if a slow- or continuous-release type of vaccine is used. This method is believed to help activate those APCs present in at or near the site of administration that may not yet have been activated by the presence of the vaccine.

In yet another embodiment, the HSP preparation is administered to a subject within a time frame of about one to about twenty-four hours before the administration of a vaccine. This method is believed to pre-activate the subject's APCs prior to the encounter with the vaccine.

A different alternative therapeutic method is also provided. In this embodiment, a mammalian (preferably human) HSP preparation is administered to a subject when it is desired that the APCs of the subject be in an activated state, such as when the subject is receiving a treatment modality that is not a vaccine. The mammalian HSP preparation can be administered regularly for a period of time, e.g., daily for up to several weeks, which may precede, overlap, and/or follow a treatment regimen with a non-vaccine modality. The HSP preparation can be administered concurrently, before, or after the administration of the treatment modality. Examples of treatment modalities include but are not limited to antibiotics, antivirals, antifungal compounds, chemotherapeutic agents, and radiation. The HSP preparation can augment the therapeutic benefit of a treatment modality and improve the outcome of the treatment. Without being bound by any theory or mechanism, the administration of a mammalian HSP preparation to a subject can enhance the responsiveness of non-specific immune mechanisms of the subject, for example, by increasing the number of natural killer (NK) cells and/or accelerating the maturation of dendritic cells.

In a preferred embodiment of the invention as provided above, the subject in whom the HSP preparation and vaccine is administered is a human.

In yet another embodiment, the invention provides a method for inducing an immune response by a vaccine composition in a subject, wherein a sub-immunogenic amount of vaccine composition is used. As used herein, a sub-immunogenic amount of a vaccine composition refers to an amount that is insufficient for inducing an immune response if the vaccine composition is administered independent of the HSP preparation. The method comprises administering to the subject an amount of a heat shock protein preparation before, concurrently with, or after the administration of the vaccine composition, such that said amount of vaccine composition effectively induces an immune response in the subject.

In yet another embodiment, the invention provides a method of activating antigen presenting cells comprising contacting APCs with a heat shock protein preparation. Prior to treatment with a heat shock protein preparation to activate the APCs, the cells can optionally be enriched or purified, and/or expanded ex vivo by methods well known in the art. The APCs can be obtained from a subject, preferably the same subject to whom the treated APCs are re-administered (i.e., autologous APCs are used), although non-autologous APCs can also be used. The non-autologous APCs can be syngeneic (i.e., from an identical twin of the individual to which the activated APCs will be administered); or allogeneic (i.e., an individual who shares at least one common MHC allele with the individual to whom the activated APCs will be administered.)

The activation of APCs can be monitored by techniques well known in the art, such as but not limited to those described in section 6 for testing $CD11b^+$ cells. In the various embodiments as above-described, in the place of a HSP preparation, activated APCs can be administered to a subject for a similar result. Accordingly, in a specific embodiment, the activated APCs can be used in vivo to produce or increase an immune response elicited by a vaccine composition which is administered to the subject at reasonably the same time. The activated APCs can alternatively be administered within a time frame of one to twenty four hours before or after the administration of a vaccine composition, or periodically for a few days or more after a slow- or continuous-release type of vaccine is used. Preferably, the treated APCs are administered to a site at or near the site of administration of the vaccine preparation. The administration of activated APCs can be conducted by any techniques known in the art.

In various embodiments of the invention, the HSP preparation may include but not limited to, hsp70, hsp90, gp96, singly or in combination with each other.

In various embodiments, the methods of the invention are used to treat or prevent any disease or disorder in which a therapeutic or prophylactic vaccine exists, i.e., that is amenable to treatment or prevention by an enhanced immune response. In specific embodiments the disease is an infectious disease, or a cancer. The heat shock protein preparation or treated APCs are generally administered separately from the vaccine composition.

The invention includes methods for producing an immune response comprises administering to the subject a vaccine composition comprising a component against which an immune response is desired to be induced; and administering to the subject a heat shock protein preparation, wherein the heat shock protein preparation does not elicit an immune response against the component in the absence of the administering of the vaccine composition.

The invention encompasses methods for treating or preventing an infectious disease in a subject comprising in any order the steps of administering to the subject a vaccine composition comprising a component that displays the antigenicity of an infectious agent that causes the infectious disease (e.g., an immunogenic amount of an antigen on the causative infectious agent); and administering to the subject an amount of a heat shock protein preparation effective in combination with the vaccine composition to induce or increase an immune response to the component in the subject, wherein the heat shock protein preparation does not elicit an immune response against said component in the absence of said administering of the vaccine composition.

The invention also encompasses methods for treating or preventing a cancer or metastasis in a subject comprising in any order the steps of administering to the subject a vaccine composition comprising a component that displays the antigenicity of a cancer cell (e.g., an immunogenic amount of an antigen on a cancer, such as but not limited to a tumor-specific antigen, and a tumor-associated antigen, or a molecule displaying antigenicity thereof); and administering to the subject an amount of a heat shock protein preparation effective to induce or increase an immune response in the subject to the component, wherein the heat shock protein preparation does not elicit an immune response against the component in the absence of the administering of the vaccine composition.

Three major families of HSPs have been identified based on molecular weight. The families have been called hsp60, hsp70 and hsp90 where the numbers reflect the approximate molecular weight of the stress proteins in kilodaltons. Many members of these families were found subsequently to be induced in response to other stressful stimuli including, but not limited to, nutrient deprivation, metabolic disruption, oxygen radicals and infection with intracellular pathogens (See Welch, May 1993, Scientific American 56-64; Young, 1990, Annu. Rev. Immunol. 8:401–420; Craig, 1993, Science 260:1902–1903; Gething, et al., 1992, Nature 355: 33–45; and Lindquist, et al., 1988, Annu. Rev. Genetics 22:631–677). A number of proteins thought to be involved in chaperoning functions are residents of the endoplasmic reticulum (ER) lumen and include, for example, protein disulfide isomerase (PDI; Gething et al., 1992, Nature 355: 33–45), calreticulin (Herbert et al., 1997, J. Cell Biol. 139:613–623), Grp94 or ERp99 (Sorger & Pelham, 1987, J. Mol. Biol. 194:(2) 341–4) which is related to hsp90, and Grp78 or BiP, which is related to hsp70 (Munro et al., 1986, Cell 46:291–300; Haas & Webl, 1983, Nature 306:387–389). It is contemplated that HSPs belonging to all of these three families, including fragments of such HSPs, can be used in the practice of the instant invention.

Heat shock proteins are among the most highly conserved proteins in existence. For example, DnaK, the hsp70 from *E. coli* has about 50% amino acid sequence identity with hsp70 proteins from excoriates (Bardwell, et al., 1984, Proc. Natl. Acad. Sci. 81:848–852). The hsp60 and hsp90 families also show similarly high levels of intra families conservation (Hickey, et al., 1989, Mol. Cell. Biol. 9:2615–2626; Jindal, 1989, Mol. Cell. Biol. 9:2279–2283). In addition, it has been discovered that the hsp60, hsp70 and hsp90 families are composed of proteins that are related to the stress proteins in sequence, for example, having greater than 35% amino acid identity, but whose expression levels are not altered by stress. Therefore it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus. The purification of stress proteins belonging to these three families is described below.

In addition, HSPs have been found to have immunological and antigenic properties. HSPs are now understood to play an essential role in immune regulation (See Mizzen, 1998, Biotherapy 10:174). For instance, prior experiments have demonstrated that HSPs stimulate strong and long-lasting specific immune responses against antigenic peptides that have been covalently or noncovalently attached to the HSPs. By utilizing a specific peptide, the immune response generated is "specific" or targeted to that peptide.

However, in the present invention, where HSP-peptide complexes are used, the peptides need not be antigenic or relevant to the condition in question. In this instance, the purpose of the invention is not to use a HSP-peptide complex to elicit a specific immune response against the bound peptide. The HSP preparations of the invention generally aid presentation of all kinds of antigens in the subject, particularly those administered to the subject in the vaccine composition.

5.1. Preparation of Heat Shock Proteins

In the present invention, purified unbound HSPS, HSPs covalently or noncovalently bound to specific peptides or nonspecific peptides (collectively referred to herein as HSP-peptide complexes), and combinations of thereof are used. Purification of HSPs in complexed or non-complexed forms are described in the following subsections.

Further, one skilled in the art can synthesize HSPs by recombinant expression or peptide synthesis, which are also described below.

5.1.1. Preparation and Purification of Hsp70 or Hsp70-Peptide Complexes

The purification of hsp70-peptide complexes has been described previously, see, for example, Udono et al., 1993, J. Exp. Med. 178:1391–1396. A procedure that may be used, presented by way of example but not limitation, is as follows:

Initially, human or mammalian cells are suspended in 3 volumes of 1× Lysis buffer consisting of 5 mM sodium phosphate buffer (pH 7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed 1 as determined by microscopic examination. As an alternative to sonication, the cells may be lysed by mechanical shearing and in this approach the cells typically are resuspended in 30 mM sodium bicarbonate (pH 7.5), 1 mM PMSF, incubated on ice for 20 minutes and then homogenized in a Dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose™ equilibrated with phosphate buffered saline (PBS) containing 2 mM $Ca^{2+}$ and 2 mM $Mg^{2+}$. When the cells are lysed by mechanical shearing the supernatant is diluted with an equal volume of 2× lysis buffer prior to mixing with Con A Sepharose™. The supernatant is then allowed to bind to the Con A Sepharose™ for 2–3 hours at 4° C. The material that fails to bind is harvested and dialyzed for 36 hours (three times, 100 volumes each time) against 10 mM Tris-Acetate (pH 7.5), 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC™ ion exchange chromatographic column (Pharmacia) equilibrated in 20 mM Tris-Acetate (pH 7.5), 20 mM NaCl, 0.1 mM EDTA and 15 mM 2-mercaptoethanol. The column is then developed with a 20 mM to 500 mM NaCl gradient and then eluted fractions fractionated by sodium dodecyl sulfate-polyacrylamide gel electrophoresis (SDS-PAGE) and characterized by immunoblotting using an appropriate anti-hsp70 antibody (such as from clone N27F3-4, from StressGen).

Fractions strongly immunoreactive with the anti-hsp70 antibody are pooled and the hsp70-peptide complexes precipitated with ammonium sulfate; specifically with a 50%–70% ammonium sulfate cut: The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephadex® G25 column (Pharmacia). If necessary the hsp70 preparation thus obtained can be repurified through the Mono Q FPLC™ ion exchange chromatographic column (Pharmacia) as described above.

The hsp70-peptide complex can be purified to apparent homogeneity using this method. Typically 1 mg of hsp70-peptide complex can be purified from 1 g of cells/tissue.

An improved method for purification of hsp70-peptide complexes comprises contacting cellular proteins with ADP or a nonhydrolyzable analog of ATP affixed to a solid substrate, such that hsp70 in the lysate can bind to the ADP or nonhydrolyzable ATP analog, and eluting the bound hsp70. A preferred method uses column chromatography with ADP affixed to a solid substratum (e.g., ADP-agarose). The resulting hsp70 preparations are higher in purity and devoid of contaminating peptides. The hsp70 complex yields are also increased significantly by about more than 10 fold. Alternatively, chromatography with nonhydrolyzable analogs of ATP, instead of ADP, can be used for purification of hsp70-peptide complexes. By way of example but not limitation, purification of hsp70-peptide complexes by ADP-agarose chromatography can be carried out as follows:

Meth A sarcoma cells (500 million cells) are homogenized in hypotonic buffer and the lysate is centrifuged at 100,000 g for 90 minutes at 4° C. The supernatant is applied to an ADP-agarose column. The column is washed in buffer and is eluted with 5 column volumes of 3 mM ADP. The hsp70-peptide complexes elute in fractions 2 through 10 of the total 15 fractions which elute. The eluted fractions are analyzed by SDS-PAGE. The hsp70-peptide complexes can be purified to apparent homogeneity using this procedure.

Separation of the HSP from an hsp70-peptide complex can be performed in the presence of ATP or low pH. These two methods may be used to elute the peptide from an hsp70-peptide complex. The first approach involves incubating an hsp70-peptide complex preparation in the presence of ATP. The other approach involves incubating an hsp70-peptide complex preparation in a low pH buffer. These methods and any others known in the art may be applied to separate the HSP and peptide from an hsp-peptide complex.

5.1.2. Preparation and Purification of Hsp90 or Hsp90-Peptide Complexes

A procedure that can be used, presented by way of example and not limitation, is as follows:

Initially, human or mammalian cells are suspended in 3 volumes of 1× Lysis buffer consisting of 5 mM sodium phosphate buffer (pH 7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate (pH 7.5), 1 mM PMSF, incubated on ice for 20 minutes and then homogenized in a Dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose™ equilibrated with PBS containing 2 mM $Ca^{2+}$ and 2 mM $Mg^{2+}$. When the cells are lysed by mechanical shearing the supernatant is diluted with an equal volume of 2× Lysis buffer prior to mixing with Con A Sepharose™. The supernatant is then allowed to bind to the Con A Sepharose™ for 2–3 hours at 4° C. The material that fails to bind is harvested and dialyzed for 36 hours (three times, 100 volumes each time) against 10 mM Tris-Acetate (pH 7.5), 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC™ ion exchange chromatographic column (Pharmacia) equilibrated with lysis buffer. The proteins are then eluted with a salt gradient of 200 mM to 600 mM NaCl.

The eluted fractions are fractionated by SDS-PAGE and fractions containing the hsp90-peptide complexes identified by immunoblotting using an anti-hsp90 antibody such as 3G3 (Affinity Bioreagents). Hsp90-peptide complexes can be purified to apparent homogeneity using this procedure. Typically, 150–200 μg of hsp90-peptide complex can be purified from 1 g of cells/tissue.

Separation of the HSP from an hsp90-peptide complex can be performed in the presence of ATP or low pH. These two methods may be used to elute the peptide from an hsp90-peptide complex. The first approach involves incubating an hsp90-peptide complex preparation in the presence of ATP. The other approach involves incubating an hsp90-peptide complex preparation in a low pH buffer. These methods and any others known in the art may be applied to separate the HSP and peptide from an hsp-peptide complex.

5.1.3. Preparation and Purification of Gp96 or Gp96-Peptide Complexes

A procedure that can be used, presented by way of example and not limitation, is as follows:

A pellet of human or mammalian cells is resuspended in 3 volumes of buffer consisting of 30 mM sodium bicarbonate buffer (pH 7.5) and 1 mM PMSF and the cells allowed to swell on ice 20 minutes. The cell pellet is then homogenized in a Dounce homogenizer (the appropriate clearance of the homogenizer will vary according to each cell type) on ice until >95% cells are lysed.

The lysate is centrifuged at 1,000 g for 10 minutes to remove unbroken cells, nuclei and other debris. The supernatant from this centrifugation step is then recentrifuged at 100,000 g for 90 minutes. The gp96-peptide complex can be purified either from the 100,000 pellet or from the supernatant.

When purified from the supernatant, the supernatant is diluted with equal volume of 2× lysis buffer and the supernatant mixed for 2–3 hours at 4° C. with Con A Sepharose™ equilibrated with PBS containing 2 mM $Ca^{2+}$ and 2 mM $Mg^{2+}$. Then, the slurry is packed into a column and washed with 1× lysis buffer until the $OD_{280}$ drops to baseline. Then, the column is washed with ⅓ column bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60–95% pure, however this depends upon the cell type and the tissue-to-lysis buffer ratio used. Then the sample is applied to a Mono Q FPLC™ ion exchange chromatographic column (Pharmacia) equilibrated with a buffer containing 5 mM sodium phosphate (pH 7). The proteins are then eluted from the column with a 0–1M NaCl gradient and the gp96 fraction elutes between 400 mM and 550 mM NaCl.

The procedure, however, may be modified by two additional steps, used either alone or in combination, to consistently produce apparently homogeneous gp96-peptide complexes. One optional step involves an ammonium sulfate precipitation prior to the Con A purification step and the other optional step involves DEAE-Sepharose™ purification after the Con A purification step but before the Mono Q FPLC™ step.

In the first optional step, described by way of example as follows, the supernatant resulting from the 100,000 g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A Sepharose™ and the procedure followed as before.

In the second optional step, described by way of example as follows, the gp96 containing fractions eluted from the Con A column are pooled and the buffer exchanged for 5 mM sodium phosphate buffer (pH 7), 300 mM NaCl by dialysis, or preferably by buffer exchange on a Sephadex G25 column. After buffer exchange, the solution is mixed with DEAE-Sepharose™ previously equilibrated with 5 mM sodium phosphate buffer (pH 7), 300 mM NaCl. The protein solution and the beads are mixed gently for 1 hour and poured into a column. Then, the column is washed with 5 mM sodium phosphate buffer (pH 7), 300 mM NaCl, until the absorbance at 280 nm drops to baseline. Then, the bound protein is eluted from the column with five volumes of 5 mM sodium phosphate buffer (pH 7), 700 mM NaCl. Protein containing fractions are pooled and diluted with 5 mM sodium phosphate buffer (pH 7) in order to lower the salt concentration to 175 mM. The resulting material then is applied to the Mono Q FPLC™ ion exchange chromatographic column (Pharmacia) equilibrated with 5 mM sodium phosphate buffer (pH 7) and the protein that binds to the Mono Q FPLC™ ion exchange chromatographic column (Pharmacia) is eluted as described before.

It is appreciated, however, that one skilled in the art may assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000 g pellet, the pellet is suspended in 5 volumes of PBS containing either 1% sodium deoxycholate or 1% oxtyl glucopyranoside (but without the $Mg^{2+}$ and $Ca^{2+}$) and incubated on ice for 1 hour. The suspension is centrifuged at 20,000 g for 30 minutes and the resulting supernatant dialyzed against several changes of PBS (also without the $Mg^{2+}$ and $Ca^{2+}$) to remove the detergent. The dialysate is centrifuged at 100,000 g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000 g supernatant, see above.

The gp96-peptide complexes can be purified to apparent homogeneity using this procedure. About 10–20 μg of gp96 can be isolated from 1 g cells/tissue.

Separation of the HSP from an gp96-peptide complex can be performed in the presence of ATP or low pH. These two methods may be used to elute the peptide from an gp96-peptide complex. The first approach involves incubating an gp96-peptide complex preparation in the presence of ATP. The other approach involves incubating an gp96-peptide complex preparation in a low pH buffer. These methods and any others known in the art may be applied to separate the HSP and peptide from an hsp-peptide complex.

5.1.4. Recombinant Expression of HSPs

Methods known in the art can be utilized to recombinantly produce HSPS. A nucleic acid sequence encoding a heat shock protein can be inserted into an expression vector for propagation and expression in host cells.

An expression construct, as used herein, refers to a nucleotide sequence encoding an HSP operably associated with one or more regulatory regions which enables expression of the HSP in an appropriate host cell. "Operably-associated" refers to an association in which the regulatory regions and the HSP sequence to be expressed are joined and positioned in such a way as to permit transcription, and ultimately, translation.

The regulatory regions necessary for transcription of the HSP can be provided by the expression vector. A translation initiation codon (ATG) may also be provided if the HSP gene sequence lacking its cognate initiation codon is to be expressed. In a compatible host-construct system, cellular transcriptional factors, such as RNA polymerase, will bind to the regulatory regions on the expression construct to effect transcription of the modified HSP sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to the HSP gene sequence or to insert the HSP gene sequence into the cloning site of a vector, linkers or adapters providing the appropriate compatible restriction sites may be ligated to the ends of the cDNAs by techniques well known in the art (Wu et al., 1987, Methods in Enzymol 152:343–349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising an HSP sequence operably associated with regulatory regions can be directly introduced into appropriate host cells for expression and production of HSP-peptide complexes without further cloning. See, for example, U.S. Pat. No. 5,580,859. The expression constructs can also contain DNA sequences that facilitate integration of the HSP sequence into the genome of the host cell, e.g., via homologous recombination. In this instance, it is not necessary to employ an expression vector comprising a replication origin suitable for appropriate host cells in order to propagate and express the HSP in the host cells.

A variety of expression vectors may be used including, but not limited to, plasmids, cosmids, phage, phagemids or modified viruses. Typically, such expression vectors comprise a functional origin of replication for propagation of the vector in an appropriate host cell, one or more restriction endonuclease sites for insertion of the HSP gene sequence, and one or more selection markers. The expression vector must be used with a compatible host cell which may be derived from a prokaryotic or an eukaryotic organism including but not limited to bacteria, yeasts, insects, mammals and humans.

For long term, high yield production of properly processed HSP or HSP-peptide complexes, stable expression in mammalian cells is preferred. Cell lines that stably express HSP or HSP-peptide complexes may be engineered by using a vector that contains a selectable marker. By way of example but not limitation, following the introduction of the expression constructs, engineered cells may be allowed to grow for 1–2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while HSP is expressed continuously.

The recombinant cells may be cultured under standard conditions of temperature, incubation time, optical density and media composition. However, conditions for growth of recombinant cells may be different from those for expression of HSPs and antigenic proteins. Modified culture conditions and media may also be used to enhance production of the HSP. For example, recombinant cells containing HSPs with their cognate promoters may be exposed to heat or other environmental stress, or chemical stress. Any techniques known in the art may be applied to establish the optimal conditions for producing HSP or HSP-peptide complexes.

5.1.5. Peptide Synthesis

An alternative to producing HSP by recombinant techniques is peptide synthesis. For example, an entire HSP, or a peptide corresponding to a portion of an HSP can be synthesized by use of a peptide synthesizer. Conventional peptide synthesis or other synthetic protocols well known in the art may be used.

Peptides having the amino acid sequence of a HSP or a portion thereof may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting HSP is accomplished using conventional procedures, such as preparative HPLC using gel permeation, partition and/or ion exchange chromatography. The choice of appropriate matrices and buffers are well known in the art and so are not described in detail herein.

5.2. Vaccines that can be Used with Heat Shock Proteins

The vaccines that can be used with the HSP or HSP-peptide complexes of the invention include but are not limited to live vaccines, inactivated vaccines, attenuated vaccines, subunit vaccines, and nucleic acid-based vaccines. Subunit vaccines may be multivalent or univalent, and may, for example, contain purified pathogen antigens, such as isolated viral coat proteins, and bacterial cell wall molecules, etc. Multivalent vaccines are made from recombinant viruses that direct the expression of more than one antigen. Until recently, vaccines are typically used for prophylaxis against infectious diseases. However, vaccines based on tumor antigens, e.g., containing tumor specific or tumor-associated antigens, have been developed for the treatment or prevention of various types of cancers. Non-limiting examples of tumor antigens that can be used in a vaccine composition may include KS 1/4 pan-carcinoma antigen (Perez and Walker, 1990, J. Immunol. 142:3662–3667; Bumal, 1988, Hybridoma 7(4):407–415); ovarian carcinoma antigen (CA125) (Yu, et al., 1991, Cancer Res. 51(2): 468–475); prostatic acid phosphate (Tailer, et al., 1990, Nucl. Acids Res. 18(16):4928); prostate specific antigen (Henttu and Vihko, 1989, Biochem. Biophys. Res. Comm. 160(2):903–910; Israeli, et al., 1993, Cancer Res. 53:227–230); melanoma-associated antigen p97 (Estin, et al., 1989, J. Natl. Cancer Inst. 81(6):445–446); melanoma antigen gp75 (Vijayasardahl, et al., 1990, J. Exp. Med. 171(4):1375–1380); high molecular weight melanoma antigen (Natali, et al., 1987, Cancer 59:55–63), the MAGE family of antigens (Hu et al., 1996, Cancer Res. 56:2479–2483; Marchand et al., 1995, Int. J. Cancer 63:883–885) and prostate specific membrane antigen. The HSP or HSP-peptide complexes of the invention can also be used with such cancer vaccines. The cancer vaccines that can be used with the methods of invention are reviewed in various publications, e.g., Pardoll, 2000, Clin. Immunol. 95(1 Pt 2): S44–62 and Stevenson, 1999, Ann Oncol. 10:1413–8 the contents of which are incorporated herein by reference in their entireties.

Many methods may be used to introduce the vaccine; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to primates, cows, horses, sheep, pigs, fowl (e.g., chickens), goats, cats, dogs, hamsters, mice and rats.

Examples of vaccine compositions that can be used with the HSP or HSP-peptide complexes of the invention include but are not limited to *bacillus* Calmette-Guerin vaccine, *brucella* strain 19 vaccine, cholera vaccine, diphtheria-tetanus toxoids-petussis vaccines, foot-and-mouth-disease vaccine, Haffkine's vaccines, various hepatitis virus vaccines, human diploid cell rabies virus, poliovirus vaccine, influenza virus vaccine, measles vaccine, measles-mumps-rubella vaccine, plague vaccine, pneumococcal vaccine, *rickettsia* vaccine, Sabin vaccine, Semple vaccine, smallpox vaccine, *staphylococcus* vaccine, typhoid vaccine, typhus vaccine, whooping cough vaccine, and yellow fever vaccine. The vaccines that can be used with the methods of invention are reviewed in various publications, e.g., The Jordan Report 2000, Division of Microbiology and Infectious Diseases, National Institute of Allergy and Infectious Diseases, National Institutes of Health, United States, the content of which is incorporated herein by reference in its entirety.

The vaccine composition may comprise adjuvants, or may be administered together with one or more adjuvants. Adjuvants that can be used include but are not limited to mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum hydroxide, aluminum phosphate gel, Freund's Complete Adjuvant, Freund's Incomplete Adjuvant, squalene or squalane oil-in-water adjuvant formulations, biodegradable and biocompatible polyesters, polymerized liposomes, triterpenoid glycosides or saponins (e.g., QuilA and QS-21, also sold under the trademark STIMULON, ISCOPREP), N-acetyl-muramyl-L-threonyl-D-isoglutamine (Threonyl-MDP, sold under the trademark TERMURTIDE), LPS, monophosphoryl Lipid A (3D-MLAsold under the trademark MPL).

5.3. Kits, Dosage Regimens, Administration and Formulations

Kits are also provided for carrying out the vaccination methods of the present invention, In a specific embodiment, a kit comprises a first container containing a heat shock protein preparation in an amount effective to increase an immune response elicited by a vaccine composition against a component of the vaccine composition against which an immune response is desired; and a second container containing the vaccine composition in an amount that, when administered before, concurrently with, or after the administration of the heat shock protein preparation in the first container, is effective to induce an immune response against the component.

Kits of the invention are provided that comprise in a container a vaccine composition in an amount effective to treat or prevent a disease or disorder; and in another container a heat shock protein preparation in an amount effective to increase or boost an immune response elicited by the vaccine. In an embodiment, the amount of vaccine composition present in the container is insufficient for inducing an immune response in a subject if administered independent of the heat shock protein preparation in the other container. The kit may optionally be accompanied by instructions.

The dosage of HSP preparation to be administered depends to a large extent on the condition and size of the subject being treated as well as the amount of vaccine composition administered, the frequency of treatment and the route of administration. Regimens for continuing therapy, including site, dose and frequency may be guided by the initial response and clinical judgment.

Depending on the route of administration and the type of HSPs in the HSP preparation, the amount of HSP in the HSP preparation can range, for example, from 0.1 to 1000 µg per administration. The preferred amounts of gp96 or hsp70 are in the range of 10 to 600 µg per administration and 0.1 to 10 µg if the HSP preparation is administered intradermally. For hsp 90, the preferred amounts are about 50 to 1000 µg per administration, and about 5 to 50 µg for intradermal administration.

In one preferred embodiment, the HSP preparation is administered concurrently with the administration of a vaccine. Concurrent administration of an HSP preparation and a vaccine means that the HSP or HSP-peptide complex is given at reasonably the same time as the vaccine. This method provides that the two administrations are performed within a time frame of less than one minute to about five minutes, or up to about sixty minutes from each other, for example, at the same doctor's visit.

Because of the administration of the HSP preparation, lesser amount of vaccine is required to elicit an immune respone in a subject. In specific embodiments, a reduction of about 10%, 20%, 30%, 40% and 50% of the amount of vaccine composition can be achieved. Even sub-immunogenic amounts of the vaccine composition can be used provided that an appropriate amount of the HSP preparation is used in conjunction. The amount of vaccine composition to be used with a HSP preparation, including amounts in the sub-immunogenic range, can be determined by dose-response experiments conducted in animal models by methods well known in the art.

Solubility and the site of the vaccination are factors which should be considered when choosing the route of administration of the HSP preparation of the invention. The mode of administration can be varied, including, but not limited to, e.g., subcutaneously, intravenously, intraperitoneally, intramuscularly, intradermally or mucosally. Mucosal routes can further take the form of oral, rectal and nasal administration. With the above factors taken into account, it is preferable to administer the HSP to a site that is the same or proximal to the site of vaccination.

In an embodiment of the invention, HSPs may be administered using any desired route of administration. Advantages of intradermal administration include use of lower doses and rapid absorption, respectively. Advantages of subcutaneous or intramuscular administration include suitability for some insoluble suspensions and oily suspensions, respectively. Mucosal routes of administration include, but are not limited to, oral, rectal and nasal administration. Preparations for mucosal administrations are suitable in various formulations as described below.

In a preferred embodiment, the invention provides for a method of introducing an HSP preparation including, but not limited to, hsp70, hsp90 and gp96 alone or in combination with each other into a subject concurrently with the administration of a vaccine at the same site or at a site in close proximity.

If the HSP preparation is water-soluble, then it may be formulated in an appropriate buffer, for example, phosphate buffered saline or other physiologically compatible solutions, preferably sterile. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, or rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such a liquid preparation may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical preparation may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

The HSP preparation for oral administration may be suitably formulated to give controlled release of the active compound.

For buccal administration, the preparation may take the form of tablets or lozenges formulated in conventional manner.

The preparation may be formulated for parenteral administration by injection, e.g., by bolus injection or continuous infusion. Formulations for injection may be presented in unit dosage form, e.g., in ampoules or in multi-dose containers, with an added preservative. The preparation may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The preparation may also be formulated in a rectal preparation such as a suppository or retention enema, e.g., containing conventional suppository bases such as cocoa butter or other glycerides.

In addition to the formulations described previously, the preparation may also be formulated as a depot preparation. Such long acting formulations may be administered by implantation (for example, subcutaneously or intramuscularly) or by intramuscular injection. Thus, for example, the preparation may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

For administration by inhalation, the preparation for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The preparation may, if desired, be presented in a pack or dispenser device which may contain one or more unit dosage forms containing the HSP preparation. The pack may for example comprise metal or plastic foil, such as a blister pack. The pack or dispenser device may be accompanied by instructions for administration.

5.4. Activation and Administration of Antigen-Presenting Cells

APC can be obtained, maintained and/or expanded by any of various methods known in the art. In one embodiment, the antigen-presenting cells, including but not limited to macrophages, dendritic cells and B-cells, can be obtained by production in vitro from stem and progenitor cells from human peripheral blood or bone marrow as described by Inaba, K., et al., 1992, J. Exp. Med. 176:1693–1702. In another embodiment, human macrophages are used, obtained from human blood cells. By way of example but not limitation, macrophages can be obtained as follows:

Mononuclear cells are isolated from peripheral blood of a patient (preferably the patient to be treated), by Ficoll-Hypaque gradient centrifugation.

Tissue culture dishes are pre-coated with the patient's own serum or with other AB+ human serum and incubated at 37° C. for 1 hr. Non-adherent cells are removed by pipetting. To the adherent cells left in the dish, is added cold (4° C.) 1 mM EDTA in phosphate-buffered saline and the dishes are left at room temperature for 15 minutes. The cells are harvested, washed with RPMI buffer and suspended in RPMI buffer. Increased numbers of macrophages can be obtained by incubating at 37° C. with macrophage-colony stimulating factor (M-CSF). In a preferred embodiment, increased numbers of dendritic cells can be obtained by incubating with granulocyte-macrophage-colony stimulating factor (GM-CSF) as described in detail by Inaba, K., et al., 1992, J. Exp. Med. 176:1693–1702.

5.4.1 Activation of Antigen Presenting Cells With HSP Preparations

APC can be activated with an HSP preparation of the invention by incubating the cells in vitro with the complexes. Preferably, the APC are activated with a HSP preparation by incubating in vitro with the hsp-complex at 37° C. for 15 minutes to 24 hours. By way of example but not limitation, $4 \times 10^7$ macrophages can be incubated with 10 microgram gp96 per ml or 100 microgram hsp90 per ml at 37° C. for 15 minutes to 24 hours in 1 ml plain RPMI medium. The cells are washed three times and resuspended in a physiological medium preferably sterile, at a convenient concentration (e.g., $1 \times 10^7$/ml) for infusion in a patient. Preferably, the patient into which the sensitized APCs are infused is the patient from which the APC were originally isolated (autologous embodiment).

5.4.2 Reinfusion of Activated APC

The activated macrophages and other APC can be reinfused into the subject by conventional clinical procedures, such as but not limited to intravenous, subcutaneous, intradermal, and intraperitoneal administration. These activated cells are reinfused, preferentially by systemic administration into the autologous patient. Subjects generally receive from about $10^6$ to about $10^{12}$ sensitized macrophages, depending on the condition of the subject.

5.5. Determination of Immunogenicity Of Vaccines after HSP Treatment

In an optional procedure, the production of or increase in immunogenicity of a vaccine that is used with the HSP preparation of the invention can be assessed using various methods well known in the art.

In one method, the immunogenicity of the vaccine and HSP preparation is determined by measuring antibodies produced in response, by an antibody assay, such as an enzyme-linked immunosorbent assay (ELISA) assay.

Methods for such assays are well known in the art (see, e.g., Section 2.1 of Current Protocols in Immunology, Coligan et al. (eds.), John Wiley and Sons, Inc. 1997). For example, microtitre plates (96-well Immuno Plate II, Nunc) are coated with 50 µl/well of a 0.75 µg/ml extract or lysate of a cancer cell or infected cell in PBS at 4° C. for 16 hours and at 20° C. for 1 hour. The wells are emptied and blocked with 200 µl PBS-T-BSA (PBS containing 0.05% (v/v) TWEEN 20 and 1% (w/v) bovine serum albumin) per well at 20° C. for 1 hour, then washed 3 times with PBS-T. Fifty µl/well of plasma or CSF from a vaccinated animal (such as a model mouse or a human patient with or without administration of a HSP preparation) is applied at 20° C. for 1 hour, and the plates are washed 3 times with PBS-T. The antigen antibody activity is then measured calorimetrically after incubating at 20° C. for 1 hour with 50 µl/well of sheep anti-mouse or anti-human immunoglobulin, as appropriate, conjugated with horseradish peroxidase diluted 1:1,500 in PBS-T-BSA and (after 3 further PBS-T washes as above) with 50 µl of an o-phenylene diamine (OPD)-$H_2O_2$ substrate solution. The reaction is stopped with 150 µl of 2M $H_2SO_4$ after 5 minutes and absorbance is determined in a photometer at 492 nm (ref. 620 nm), using standard techniques.

In another method, the "tetramer staining" assay (Altman et al., 1996, Science 274: 94–96) may be used to identify antigen-specific T-cells. For example, in one embodiment, an MHC molecule containing a specific peptide antigen, such as a tumor-specific antigen, is multimerized to make soluble peptide tetramers and labeled, for example, by complexing to streptavidin. The MHC-peptide antigen complex is then mixed with a population of T cells obtained from a patient treated with a vaccine and the HSP preparation. Biotin is then used to stain T cells which express the tumor-specific antigen of interest.

Furthermore, using the mixed lymphocyte target culture assay, the cytotoxicity of T cells can be tested in a 4 hour $^{51}$Cr-release assay (see Palladino et al., 1987, Cancer Res. 47:5074–5079). In this assay, the mixed lymphocyte culture is added to a target cell suspension to give different effector: target (E:T) ratios (usually 1:1 to 40:1). The target cells are pre-labeled by incubating $1 \times 10^6$ target cells in culture medium containing 500 µCi of $^{51}$Cr per ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm. In order to block the MHC class I cascade a concentrated hybridoma supernatant derived from K-44 hybridoma cells (an anti-MHC class I hybridoma) is added to the test samples to a final concentration of 12.5%.

Alternatively, the ELISPOT assay can be used to measure cytokine release in vitro by cytotoxic T cells after stimulation with vaccine and HSP preparation. Cytokine release is detected by antibodies which are specific for a particular cytokine, such as interleukin-2, tumor necrosis factor α or interferon-γ (for example, see Scheibenbogen et al., 1997, Int. J. Cancer, 71:932–936). The assay is carried out in a microtitre plate which has been pre-coated with an antibody specific for a cytokine of interest which captures the cytokine secreted by T cells. After incubation of T cells for 24–48 hours in the coated wells, the cytotoxic T cells are removed and replaced with a second labeled antibody that recognizes a different epitope on the cytokine. After extensive washing to remove unbound antibody, an enzyme substrate which produces a colored reaction product is added to the plate. The number of cytokine-producing cells is counted under a microscope. This method has the advantages of short assay time, and sensitivity without the need of a large number of cytotoxic T cells.

5.6. Treatment and Prevention of Infectious Diseases

Infectious diseases that can be treated or prevented by use of a vaccine composition in conjunction with the methods of the present invention are caused by infectious agents including, but not limited to, viruses, bacteria, fungi protozoa and parasites. Some of the commonly-used vaccine compositions against infectious diseases are described in Section 5.2. Other examples are described in The Jordan Report 2000, Division of Microbiology and Infectious Diseases, National Institute of Allergy and Infectious Diseases, National Institutes of Health, United States, the content of which is incorporated herein by reference in its entirety.

Viral diseases that can be treated or prevented by use of a vaccine composition in conjunction with the methods of the present invention include, but are not limited to, those caused by hepatitis A virus, hepatitis B virus, hepatitis C virus, influenza, varicella, adenovirus, herpes simplex I virus, herpes simplex II virus, rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, human immunodeficiency virus type I (HIV-I), and human immunodeficiency virus type II (HIV-II).

Bacterial diseases that can be treated or prevented by use of a vaccine composition in conjunction with the methods of the present invention are caused by bacteria including, but not limited to, mycobacteria *rickettsia*, mycoplasma, *neisseria* and *legionella*.

Protozoal diseases that can be treated or prevented by use of a vaccine composition in conjunction with the methods of the present invention are caused by protozoa including, but not limited to, *leishmania*, kokzidioa, and *trypanosoma*.

Parasitic diseases that can be treated or prevented by use of a vaccine composition in conjunction with the methods of the present invention are caused by parasites including, but not limited to, chlamydia and *rickettsia*.

5.7. Treatment of Cancer

A number of cancer vaccines for treatment of melanoma, pancreatic carcinoma, breast cancer, prostate cancer are currently in clinical trials. The HSP preparation can be used in conjunction with such cancer vaccines for the treatment and prevention of the respective types of cancers. Examples of cancer vaccines that can be used with the methods of invention are described in various publications, e.g., Pardoll, 2000, Clin. Immunol. 95(1 Pt 2): S44-62 and Stevenson, 1999, Ann Oncol. 10:1413–8.

Cancers that can also be treated by use of a vaccine composition in conjunction with the methods of the present invention include, but are not limited to the following types of cancer: human sarcomas and carcinomas, e.g., fibrosarcoma, myxosarcoma, liposarcoma, echondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

6. EXAMPLE

Heat Shock Protein Activates Antigen Presenting Cells

Antigen presenting cells (APCs), such as dendritic cells, B cells, and macrophages, are key components of innate and adaptive immune responses. They are normally quiescent and require activation for their function. The identity of signals which activate APCs is thus a crucial question. Apparently, necrotic but not apoptotic cell death leads to release of HSPs. Applicant's experimentation with CD11b$^+$ cells as shown in this section reveals that increased concentration of HSPs in the extracellular milieu where there are APCs induces secretion of cytokines and upregulates surface expression of antigen-presenting and co-stimulatory molecules, including, but not limited to, B7-1, B7-2, and MHC class II. HSPs interact with these APCs through the conserved NFκB pathway. During antigen presentation, the complementary ligands on the T cells that associate with B7-1, B7-2, and MHC class II are CD28, CD28, and T-cell antigen surface receptors (TCRs) with CD4, respectively (See Banchereau, 1998, Nature 392:247).

Thus, HSPs have been identified to constitute a signal for APC activation.

6.1. Materials and Methods

HSPs, and Antibodies. Hsp90, hsp70 and gp96 were purified simultaneously from C57BL/6 mouse liver as described (8). Antibodies against CD80 (B7-1), CD86 (B7-2), CD40, CD11b, and MHC II for FACS analysis were purchased from Pharmingen, San Diego, Calif.

Assay of LPS content. The LPS content was measured by the LAL assay (LAL Kit QCL-1000, BIOWHITTAKER, Walkersville, Md.).

Preparation of necrotic and apoptotic cells. Cells were frozen and thawed through four cycles of liquid nitrogen-room temperature treatments, in order to mimic necrosis. Cells were irradiated (7,500 rads) in order to initiate apoptosis.

Generation of bone marrow derived DCs. Femurs and tibia of C57BL/6 mice were removed. The marrow was flushed out from the bones with media and leukocytes obtained were cultured as described (Lutz et al., 1999, J. Immunol. Methods, 223:77–92).

Cytokine assay. Cells ($5 \times 10^4$) were incubated for 20 hours at 37° C. in complete medium with 5% fetal calf serum, or with increasing quantities of HSPs, in 96 well, flat bottom plates. Supernatants were harvested and assayed by ELISA for TNF-α, IL12, IL-1β, GM-CSF and Interferon-γ (IFN-γ). IL-1β, TNF-α, GM-CSF and IFN-γ kits were purchased from Endogen Inc., Woburn, Mass., IL12 kit was purchased from R&D Systems, Inc., Minneapolis, Minn.

Preparation of nuclear extracts and Electrophoretic mobility shift assay. APCs were washed with PBS (LPS-free) and re-suspended in cold lysis buffer [buffer A: 10 mM Hepes (pH 7.9), 10 mM KCl, 0.1 mM EDTA, 0.1 mM EGTA, 1 mM DTT, 0.5 mM PMSF, 1 μM aprotinin, 1 μM pepstatin and 14 μM leupeptin] with 0.1% NP40 and incubated on ice for 30 min. Nuclei were pelleted at 14000 rpm for 2 min at 4° C. Supernatant was collected and protein concentration was measured by Bradford assay. The standard DNA-binding reaction was performed using κB DNA probe (5'-AGTTGAGGGGACTTTCCCAGGC-3'), as described by Dignam et al. (1983, Nucleic Acids Res. 11:1475–89).

6.2. Necrotic but not Apoptotic Cells Release HSPs

Cell death can be achieved in a variety of ways, popularly classified into two: apoptotic and necrotic. The inventors investigated which of these two forms of death can result in release of the major HSPs hsp70, hsp90, calreticulin (CRT) and gp96. E.G7 cells were subjected to a freeze-thaw procedure as a necrosis-mimetic or were irradiated as a form of apoptosis-mimetic process, as described in Methods. Cells were checked for necrosis visually under the microscope, and for apoptosis, by externalization of phosphatidyl serine (as detected by staining with Annexin V) and degradation of PARP by caspases (Schletter et al., 1995, Arch. Microbiol. 164:383–9). The supernatants of the treated cells were collected immediately after treatment or 24 hours after treatment by either method and analyzed by SDS-PAGE and immunoblotting with antibodies to the 4 HSPs. It was observed that necrotic but not apoptotic death led to release of all four HSPs. No Hsps were detected in the supernatants of apoptotic cells even 24 hours after death.

6.3. Activation of CD11b+ Cells by Heat Shock Proteins

Three representative HSPs, hsp90 and gp96 (of the hsp90 family) and hsp70 were tested for their abilities to activate antigen presenting cells. Hsp90 and hsp70 are cytosolic proteins whereas gp96 is localized in the endoplasmic reticulum. Altogether, the three HSPs constitute the most abundant soluble components (>2% of the total protein) of the mammalian cells. Approximately 30 µg gp96, 200 µg hsp70 and 400 µg hsp90 can be isolated in purified form from $2-5\times10^8$ cells. The three HSPs were purified from livers of C57BL/6 mice as described below were shown to be homogenous by SDS-polyacrylamide gel electrophoresis (FIG. 1A) and were identified by immunoblotting with respective monoclonal antibodies. Peritoneal cells from naïve mice or mice previously injected intraperitoneally with pristane were positively selected for CD11b+ cells as described, which were then cultured in vitro with increasing quantities of gp96 for 20 hours at 37° C. Supernatants were harvested and tested for the presence of IL-1β, TNF-α, GM-CSF, IL-12 and interferon-γ (as a negative control) by ELISA (FIG. 1B). Treatment with anti-CD11b antibody during or after positive selection did not result in activation of cells. Gp96 was found to activate, in a titratable manner, secretion of all the cytokines tested, except interferon-γ. Similar results were obtained with hsp90 and hsp70 (FIG. 1C). Although gp96 was the most potent inducer of the four cytokines at comparable protein quantities, it is the least abundant among the HSPs tested. Hsp90 appears to be the most significant stimulator on a per cell equivalent basis when one considers that hsp90 is the most abundant among the HSPs. In addition, the ability of non-HSPs such as histone, ovalbumin and insulin was also tested in the same buffers as the HSPs, gp96, hsp90 or hsp70. No stimulation of cytokine release was elicited by these non-HSP's (FIG. 1D).

6.4. Ability to Activate CD11b+Cells Does Not Derive from LPS

As LPS is a known and potent stimulator of APCs and as LPS may contaminate buffers, the possibility that contaminating LPS may be responsible for the observed effects was tested, even though the HSP preparations used in the experiments shown in FIG. 1 were isolated from a mammalian source under clean conditions. Mice of the C3H/HeJ strain are known to be hypo-responsiveness to LPS and the ability of CD11b+ cells from these mice and their LPS-responsive counterparts, the C3H/HeN mice, was tested. It was observed that similar to LPS, gp96 preparations failed to stimulate CD11b+ cells from the C3H/HeJ strain to secrete TNF-α or IL-1β (FIG. 2). At first look, these observations suggested that the APC-activating activity of HSP preparations was derived from contaminating LPS.

In order to explore the contribution of LPS more rigorously, HSPs were purified by the deliberate use of LPS-free reagents and Good Manufacturing Practices of the US Food and Drug Administration and the resulting HSP preparations were tested and shown to be free of detectable levels of LPS (<0.02 e.u.) by *Limulus amebocyte* lysate (LAL) assay. The LPS-free HSP preparations still stimulated CD11b+ cells to secrete cytokines as shown in FIG. 3A. As the lowest detection limit of LPS in the LAL assay in our hands was 0.02 e.u., this quantity of LPS and ten times higher quantities of LPS were tested for their ability to activate APCs. These quantities were found to be too low to stimulate the APCs to release either of the two cytokines tested (FIG. 3A). Far larger quantities of LPS, i.e. 1000 e.u./ml were necessary to stimulate the CD11b+ cells under the conditions used in our experiments (FIG. 3A). This is not a large quantity of LPS in itself, and is comparable to the quantities used in previous studies for activation of APCs. As additional control, under conditions where increasing quantities of gp96 induced the release of increasing levels of TNF-α and IL-β (i.e. under linear conditions of the assay), twice the highest quantity of serum albumin prepared in the same buffer as gp96, did not lead to release of detectable levels of either cytokine (FIG. 3A).

The effect of LPS was tested in another manner. Activation of APCs by LPS is dependent upon the presence of the LPS-binding protein (LBP) normally present in serum. The LBP concentrates LPS and delivers it to CD14 molecules on the APC surface thus permitting relatively low concentrations of LPS to activate APCs. The LBP-dependence is less pronounced or absent at high LPS concentrations. In order to distinguish the roles of LPS and HSPs in APC-activation, serum dependence of each activity was tested. The adherent fraction of the PECs (over 90% CD11b+) of C57BL/6 mice was simulated with titrated quantities of gp96 or LPS preparations in the presence or absence of serum and the supernatants were tested for the presence of IL-β. It was observed (FIG. 3B) that while LPS preparations were significantly dependent on the presence of serum, the ability of gp96 preparations to stimulate APCs to secrete IL-β was entirely unaffected by serum. These considerations ruled out the possibility that the observed activation of CD11b+ cells by HSP preparations is not due to LPS contaminants in the preparation but is inherent in the HSPs themselves.

The effect of LPS was tested in yet another manner by using an antagonist (competitive inhibitor) of LPS (Rslp), derived from *Rhodopseudomonas spheroides* (Henricson et al., 1992, Infect Immun., 60:4285–90). This inhibitor diminished the ability of LPS but not gp96 to stimulate secretion of IL-1 by >75%. In fact, the activity of gp96 was greater in the presence of Rslp (FIG. 3C).

6.5. HSPs Stimulate Expression of Antigen Presenting and Costimulatory Molecules The effect of HSPs on maturation of dendritic cells (DCs) was examined. Homogenous, LPS-free preparations of the HSPs gp96 and hsp70 were obtained from livers of C57BL/6 mice. Bone marrow-derived DCs, obtained from culturing in GM-CSF-containing medium, were pulsed with gp96, hsp70, or LPS (as a positive control) or serum albumin (as a negative control). The pulsed DCs were tested for surface expression of MHC 11, B7.1, B7.2 and CD40 molecules. LPS induced expression of all markers tested. Gp96 (400 µg/ml) was observed to induce a high degree of expression of MHC II and the co-stimulatory molecule B7.2, but not B7.1 nor CD40 (FIG. 4). Hsp70 (400 µg/ml), on the other hand, elicited a modest stimulation of surface expression of B7.2 but not B7.1, nor MHC 11 and CD40. The complete lack of stimulation of CD40 expression by gp96 or hsp70 led us to test this phenomenon more extensively and at a range of concentrations of the HSPs (40–400 µg/ml); however, CD40 expression was not induced at any concentration tested. Serum albumin (400 µg/ml), in the same buffer as the HSPs, did not induce expression of any of the markers tested.

6.6. HSPs Activates Translocation of NF-KB

The mechanism through which gp96 interacts with APCs was investigated, with reference to the activation of the NFκB pathway, shown previously (Ghosh et al., 1998, Ann. Rev. Immunol. 16:225–260) to be a key transcriptional regulator for several cytokines and other immunologically important molecules. This pathway has also been shown to be activated in response to LPS and to be involved in the maturation of dendritic cells (Rescigno et al., 1998, J. Exp. Med. 188:2175–2180). Primary cultures of CD11c$^+$ cells were pulsed with gp96 or LPS and cells were harvested at various time intervals. Nuclear extracts from the samples were used for binding to NFκB-specific oligomers and were resolved by native PAGE. It was observed the gp96 activates the transduction pathway and does so with a kinetics distinctly different from that of LPS (FIG. 5). The nuclear translocation of NFκB is seen in gp96-treated dendritic cells (DCs) as early as 15 minutes after pulsing and the signal diminishes to background levels by 120 minutes. In contrast, the translocation in LPS-treated DCs has a slower initiation kinetics. The differences in the kinetics of translocation of NFκB between gp96 and LPS as seen here is not a function of the quantities of either agent. Exposure of DCs to graded quantities of each shows the same differences in kinetics. In addition to providing a key glimpse into the mechanism through which HSPs activate APCs, these studies show the extent to which the effects of LPS and HSPs on APCs are similar yet distinct.

In view of the data shown in FIG. 5, and in view of the recent demonstration by Gallucci et al. (1999, Nat. Med. 5:1249–55) and Sauter et al. (2000, J. Exp. Med. 191: 423–434) the necrotic but not apoptotic cells mediate maturation of DCs, we tested whether exposure of DCs to necrotic or apoptotic cells leads to translocation of NFκB to the nucleus. Cultures of immature DCs were exposed to necrotic or apoptotic E.G7 cells (prepared as described in Methods), and were monitored for expression of MHC 11, B7.1, B7.2 and CD40. Exposure of DCs to necrotic but not apoptotic cells elicited expression of several maturation markers on the DCs (FIG. 6A), and also elicited translocation of NFκB to the nucleus (FIG. 6B).

6.7. Discussion

HSPs are intracellular molecules and the physiological relevance of their ability to activate APCs may not be immediately obvious. However, being the most abundant, soluble, intracellular molecules, the presence of HSPs in the extracellular milieu would act an excellent message alerting the APCs to physical damage of the surrounding cells, whether as a consequence of bacterial and viral infections or mechanical injury. The ability of this signal to activate APCs can therefore be easily considered to confer an immunological, and hence survival advantage to the organism. The co-segregation of immunogenicity of a variety of cancers with higher levels of expression of inducible hsp70, without any preceding change in the antigenic repertoire of the cancers, is a case in point (1995, Menoret et al., J. Immunol., 155:740–7; 1998, Melcher et al., Nat. Med., 5:581–7). Conversely, the lack of such a signal may provide a mechanism for discrimination between the presence of antigen with and without 'danger', as proposed in Fuchs and Matziner (1996, Semin. Immunol., 8:271–80). The quantities of HSPs shown here to be necessary to stimulate APCs in vitro are well within the range expected to be released locally as a result of cell lysis in vivo. Typically, 1 g of tissue yields approximately 30 µg gp96, 200 µg hsp70 and 400 µg hsp90. These recoveries are somewhere in the range of 25%. Thus, 1 g of tissue contains ~2.5 mg HSPs. Considering that the tissue lysis in vivo can be reasonably assumed to happen not in solution but in a semi-liquid physical state, lysis of as little as 1 mg of cells (approximately $10^5$–$10^6$ cells, depending on the cell type) will lead to release of ~2 µg HSP in a volume of ~1–2 µl or less. That is a concentration of 1–2 mg/ml—a higher concentration than that used in the described studies in vitro. Considerations of quantity are therefore compatible with a role in vivo, of HSPs in activation of APCs.

Examination of the levels of cytokines released by DCs, or of the extent of induction of the maturation markers on DCs by stimulation with HSPS, shows that the HSPs stimulate the DCs to a modest degree, as compared with the stimulation conferred by LPS. For this reason, the inventors have tested the observations repeatedly in as many as ten experiments and have found them to be consistent. The inventors infer that the endogenous activators of DCs (HSPs in this instance) are much slower activators than external activators such as LPS for a physiological reason the lower 'specific activity' of endogenous signals allows for a more regulated activity, as the response to an internal signal might have to be far more modulated and more titratable, than that to an external signal.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method of treating a cancer in a subject in need of said treating comprising the steps of:
   (a) administering to the subject a composition comprising a component that displays the antigenicity of a cancer cell; and
   (b) administering to the subject an amount of a purified heat shock protein preparation, wherein the heat shock protein preparation comprises purified i) unbound heat shock protein, or ii) heat shock protein bound to a molecule that does not display the immunogenicity of the component.

2. The method according to claim 1 wherein the heat shock protein preparation comprises a heat shock protein selected from the group consisting of hsp70, hsp90, gp96, calreticulin, and a combination of any two or more thereof.

3. The method according to claim 1 wherein the heat shock protein preparation comprises purified heat shock protein bound to a molecule that does not display the immunogenicity of the component.

4. The method according to claim 1 wherein the heat shock protein preparation comprises purified unbound heat shock protein.

5. The method according to claim 1 wherein the heat shock protein preparation comprises heat shock protein bound to a molecule that does not display the immunogenicity of the component and purified unbound heat shock protein.

6. The method according to claim 1 wherein the subject is human and the heat shock protein preparation comprises mammalian heat shock protein.

7. The method according to claim 1 wherein the heat shock protein preparation is administered before the administration of the composition.

8. The method according to claim 1 wherein the heat shock protein preparation is administered concurrently with the administration of the composition.

9. The method according to claim 1 wherein the heat shock protein preparation is administered after the administration of the composition.

10. The method according to claim 1 wherein the heat shock protein preparation is administered before the administration of the composition.

11. The method according to claim 2 wherein the heat shock protein preparation is administered concurrently with the administration of the composition.

12. The method according to claim 2 wherein the heat shock protein preparation is administered after the administration of the composition.

13. The method according to claim 3 wherein the heat shock protein preparation is administered before the administration of the composition.

14. The method according to claim 3 wherein the heat shock protein preparation is administered concurrently with the administration of the composition.

15. The method according to claim 3 wherein the heat shock protein preparation is administered after the administration of the composition.

16. The method according to claim 4 wherein the heat shock protein preparation is administered before the administration of the composition.

17. The method according to claim 4 wherein the heat shock protein preparation is administered concurrently with the administration of the composition.

18. The method according to claim 4 wherein the heat shock protein preparation is administered after the administration of the composition.

19. The method according to claim 5 wherein the heat shock protein preparation is administered before the administration of the composition.

20. The method according to claim 5 wherein the heat shock protein preparation is administered concurrently with the administration of the composition.

21. The method according to claim 5 wherein the heat shock protein preparation is administered after the administration of the composition.

22. The method according to claim 5 wherein the heat shock protein preparation and the composition are both administered on the same day.

23. The method of claim 1 or 6 wherein the component is a tumor antigen.

24. The method according to claim 1 wherein the cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia, acute lymphocytic leukemia, acute myelocytic leukemia, myeloblastic leukemia, promyelocytic leukemia, myelomonocytic leukemia, monocytic leukemia, erythroleukemia leukemia, chronic leukemia, chronic myelocytic leukemia, granulocytic leukemia, chronic lymphocytic leukemia, polycythemia vera, lymphoma, Hodgkin's disease lymphoma, non-Hodgkin's disease lymphoma, multiple myeloma, Waldenström's macroglobulinemia, and heavy chain disease.

25. The method according to claim 3 wherein the heat shock protein preparation and the composition are both administered on the same day.

26. The method of claim 4 wherein the heat shock protein preparation and the composition are both administered on the same day.

27. The method of claim 1 or 6 wherein the component is a KS 1/4 pan-carcinoma antigen, an ovarian carcinoma antigen, a prostatic acid phosphate, a prostate specific antigen, a melanoma-associated antigen p97, a melanoma antigen gp75, a high molecular weight melanoma antigen, a MAGE family of antigens antigen, or a prostate specific membrane antigen.

28. The method of claim 1 or 6 wherein the component is a protein subunit.

29. The method according to claim 1 or 6 wherein the heat shock protein preparation comprises a purified population of heat shock protein bound to molecules that do not display the immunogenicity of the component.

30. The method according to claim 4 wherein the heat shock protein preparation comprises purified unbound heat shock proteins that are a combination of two or more heat shock proteins.

31. The method according to claim 1 or 6 wherein the heat shock protein preparation comprises (a) a population of heat shock protein bound to molecules that do not display the immunogenicity of the component, and (b) purified unbound heat shock proteins.

32. The method according to any one of claims 1, 2, 3, 4, 5, 6–22, 24, 25, or 30, wherein the heat shock protein preparation is administered to the subject in an amount effective to induce or increase an immune response in the subject to the component.

33. The method according to claim 23 wherein the heat shock protein preparation is administered to the subject in an amount effective to induce or increase an immune response in the subject to the component.

34. The method according to claim 1 or 2 wherein the heat shock protein preparation is administered to the subject in an amount effective to induce or increase an immune response in the subject to the component.

35. The method according to claim 6 wherein the heat shock protein preparation is administered to the subject in an amount effective to induce or increase an immune response in the subject to the component.

36. The method according to claim 23 wherein the heat shock protein preparation is administered to the subject in an amount effective to induce or increase an immune response in the subject to the component.

37. The method according to claim 27 wherein the heat shock protein preparation is administered to the subject in an amount effective to induce or increase an immune response in the subject to the component.

38. The method according to claim 28 wherein the heat shock protein preparation is administered to the subject in an amount effective to induce or increase an immune response in the subject to the component.

39. The method of claim 23 wherein the component is a tumor-associated antigen.

40. The method of claim 23 wherein the component is a tumor specific antigen.

41. The method of claim 1 or 6 wherein heat shock protein in the heat shock protein preparation is present in an amount ranging from 0.1 µg to 1000 µg per administration.

42. The method of claim 1 or 6 wherein heat shock protein in the heat shock protein preparation is gp96 or hsp70 and is present in an amount ranging from 10 µg to 600 µg per administration.

43. The method of claim 1 or 6 wherein heat shock protein in the heat shock protein preparation is gp96 or hsp70, said administering is intradermal, and said heat shock protein is present in an amount ranging from 0.1 µg to 10 µg per administration.

44. The method of claim 1 or 6 wherein heat shock protein in the heat shock protein preparation is hsp90, and is present in an amount ranging from 50 µg to 1000 µg per administration.

45. The method of claim 1 or 6 wherein the heat shock protein in the heat shock protein preparation is hsp90, said administering is intradermal, and said heat shock protein is present in an amount ranging from 5 µg to 50 µg per administration.

46. The method according to claim 29 wherein the heat shock protein preparation is administered to the subject in an amount effective to induce or increase an immune response in the subject to the component.

47. The method according to claim 31 wherein the heat shock protein preparation is administered to the subject in an amount effective to induce or increase an immune response in the subject to the component.

48. The method of claim 1 or 2 wherein the heat shock protein preparation and the composition are both administered on the same day.

49. The method of claim 1, 2, 6, or 24 wherein the heat shock protein preparation comprises purified heat shock protein bound to a molecule that does not display the immunogenicity of said cancer.

* * * * *